US009625481B2

(12) United States Patent
Mellars et al.

(10) Patent No.: US 9,625,481 B2
(45) Date of Patent: Apr. 18, 2017

(54) NON-CONTACT OPTICAL ENCODING SCHEME FOR INTELLIGENT AUTOMATION PUCK

(71) Applicants: Colin Mellars, Dover, NJ (US); Baris Yagci, Whippany, NJ (US); Benjamin Samuel Pollack, Budd Lake, NJ (US)

(72) Inventors: Colin Mellars, Dover, NJ (US); Baris Yagci, Whippany, NJ (US); Benjamin Samuel Pollack, Budd Lake, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 14/402,974

(22) PCT Filed: May 21, 2013

(86) PCT No.: PCT/US2013/042022
§ 371 (c)(1),
(2) Date: Nov. 21, 2014

(87) PCT Pub. No.: WO2013/177163
PCT Pub. Date: Nov. 28, 2013

(65) Prior Publication Data
US 2015/0140668 A1 May 21, 2015

Related U.S. Application Data

(60) Provisional application No. 61/651,296, filed on May 24, 2012.

(51) Int. Cl.
G01N 35/04 (2006.01)
G01N 35/02 (2006.01)
B01L 3/00 (2006.01)
B01J 19/00 (2006.01)
G01N 35/00 (2006.01)
G05D 1/02 (2006.01)

(52) U.S. Cl.
CPC ....... *G01N 35/04* (2013.01); *G01N 35/00732* (2013.01); *G01N 35/00871* (2013.01); *G05D 1/0234* (2013.01); *B01J 19/0093* (2013.01); *B01L 3/54* (2013.01); *G01N 2035/00772* (2013.01); *G01N 2035/00792* (2013.01); *G01N 2035/00831* (2013.01); *G01N 2035/0406* (2013.01); *G01N 2035/0432* (2013.01); *G01N 2035/0467* (2013.01); *G01N 2035/0489* (2013.01); *G01N 2035/0491* (2013.01); *G01N 2035/0494* (2013.01); *G05D 2201/0216* (2013.01); *Y10T 436/115831* (2015.01)

(58) Field of Classification Search
CPC ................ Y10T 436/00; Y10T 436/11; Y10T 436/113332; G01N 35/04; G01N 35/02; G01N 35/00; G01N 2035/0491; G01N 2035/0494; G01N 2035/0474; G01N 2035/04; G01N 2035/02; G01N 2035/00; B01J 19/0093; B01J 19/00; B01L 3/54; B01L 3/52
USPC ............................ 436/50, 43; 422/67, 63, 50
See application file for complete search history.

(56) References Cited

U.S. PATENT DOCUMENTS

| 4,259,290 A | 3/1981 | Suovaniemi et al. |
| 6,429,016 B1 | 8/2002 | McNeil |
| 2006/0040341 A1 | 2/2006 | Bland et al. |
| 2006/0115133 A1 | 6/2006 | Potter et al. |
| 2009/0017491 A1 | 1/2009 | Lemme et al. |
| 2010/0025464 A1 | 2/2010 | Trueeb et al. |
| 2013/0034410 A1* | 2/2013 | Heise et al. ............. 414/222.13 |
| 2014/0305227 A1 | 10/2014 | Johns |

FOREIGN PATENT DOCUMENTS

| WO | WO 2011/138448 A1 * | 11/2011 | ............... B65G 1/04 |
| WO | 2012/158520 A1 | 11/2012 | |
| WO | 2013/116651 A1 | 8/2013 | |

OTHER PUBLICATIONS

Beacon definition, Merriam-Webster, http://www.merriam-webster.com/dictionary/beacon, obtained on Sep. 2, 2016, pp. 1-9.*
Beacon definition, Dictionary.com, http://www.dictionary.com/browse/beacon, obtained on Sep. 2, 2016, pp. 1-6.*
PCT International Search Report and Written Opinion dated Oct. 4, 2013 (14 Pages).
Extended EP Search Report dated Jan. 5, 2016 of corresponding European Application No. 13794585.3, 5 Pages.

* cited by examiner

Primary Examiner — Christine T Mui

(57) ABSTRACT

An automation system for an in vitro diagnostics environment includes a plurality of intelligent carriers that include onboard processing and navigation capabilities. The intelligent carriers can include one or more image sensors to observe the relative motion of the track as the carrier traverses it. The carriers can also observe position marks on the track surface to provide absolute position information, which can include additional data, such as routing instructions. Synchronization marks may be provided to correct errors in the observed trajectory.

20 Claims, 18 Drawing Sheets

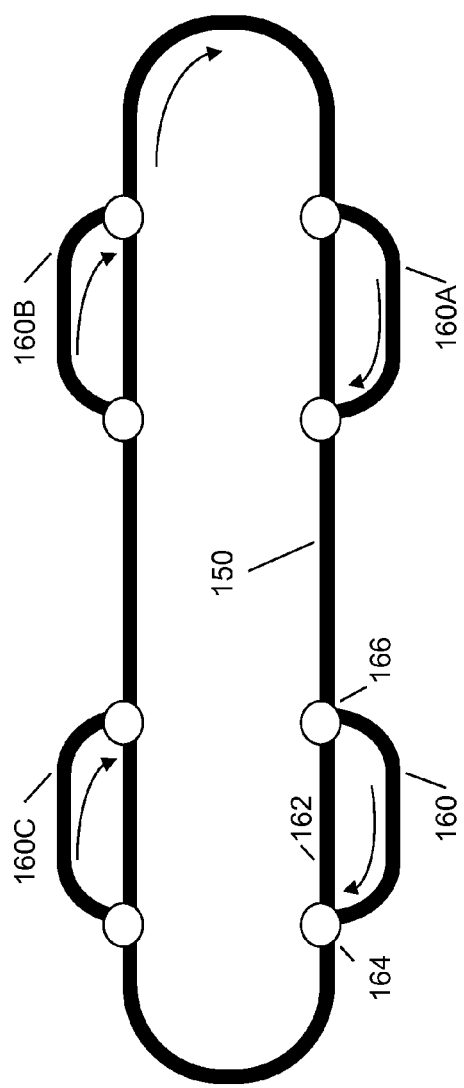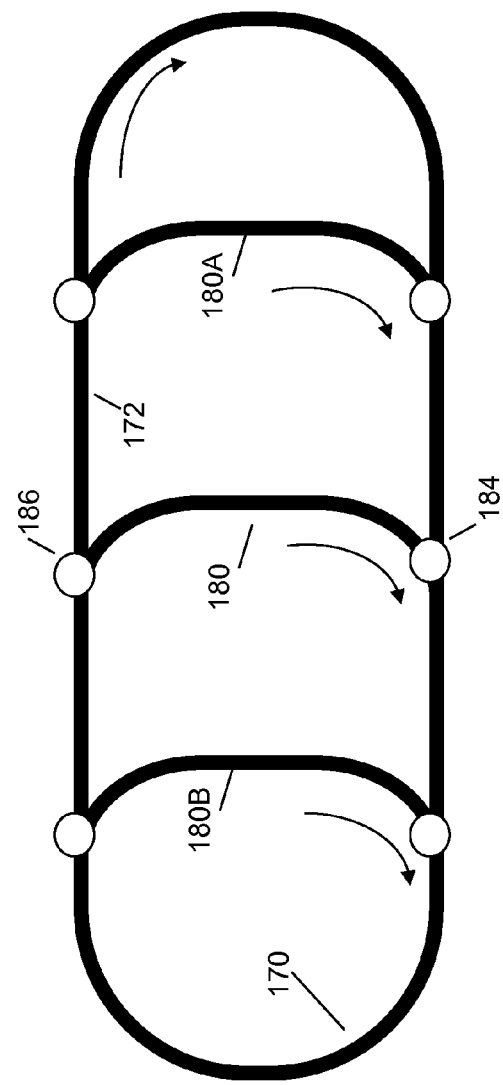

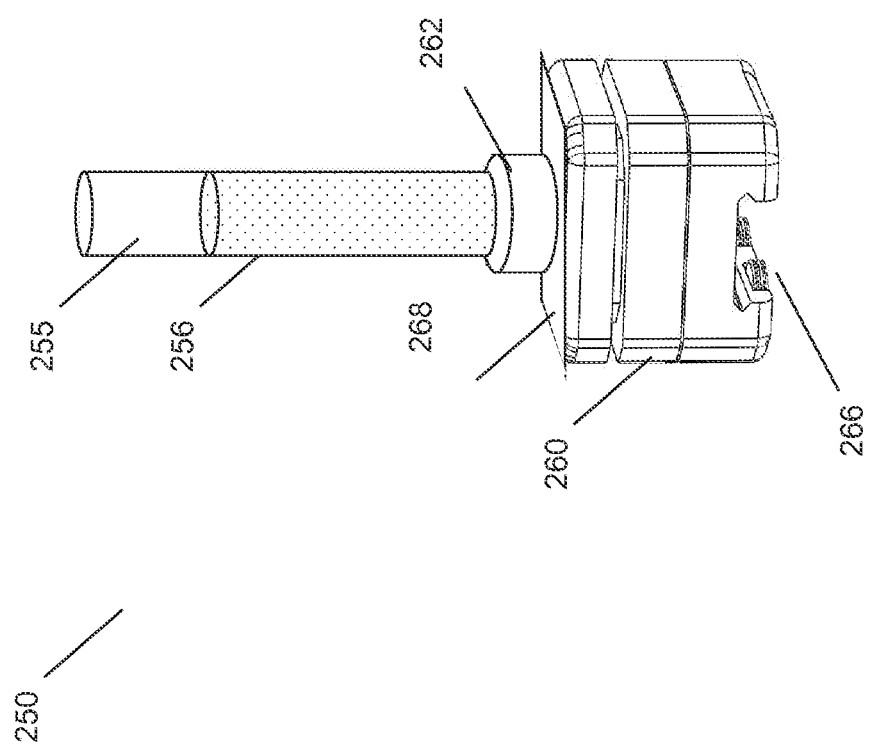

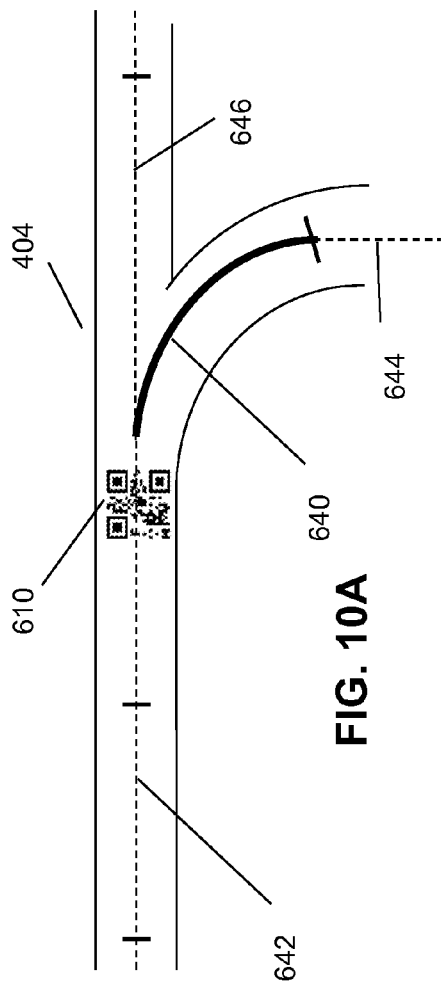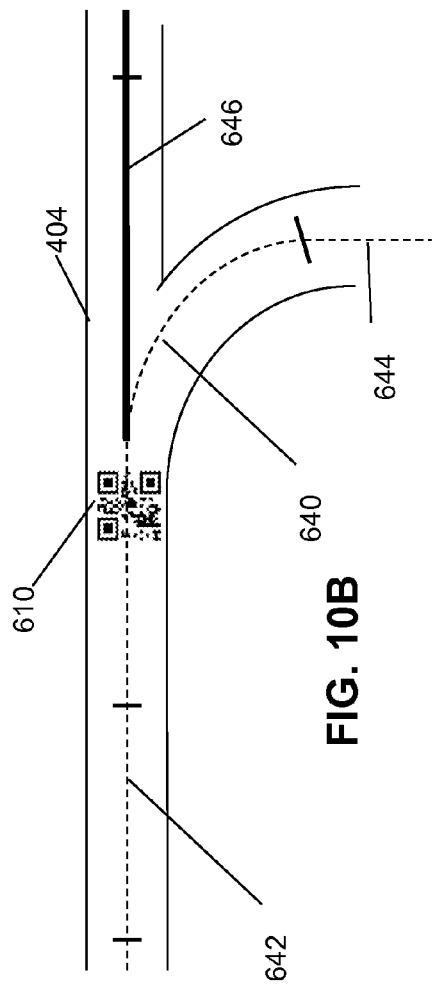

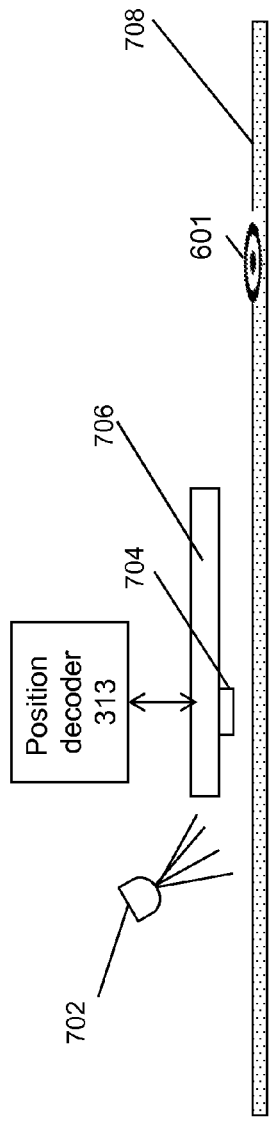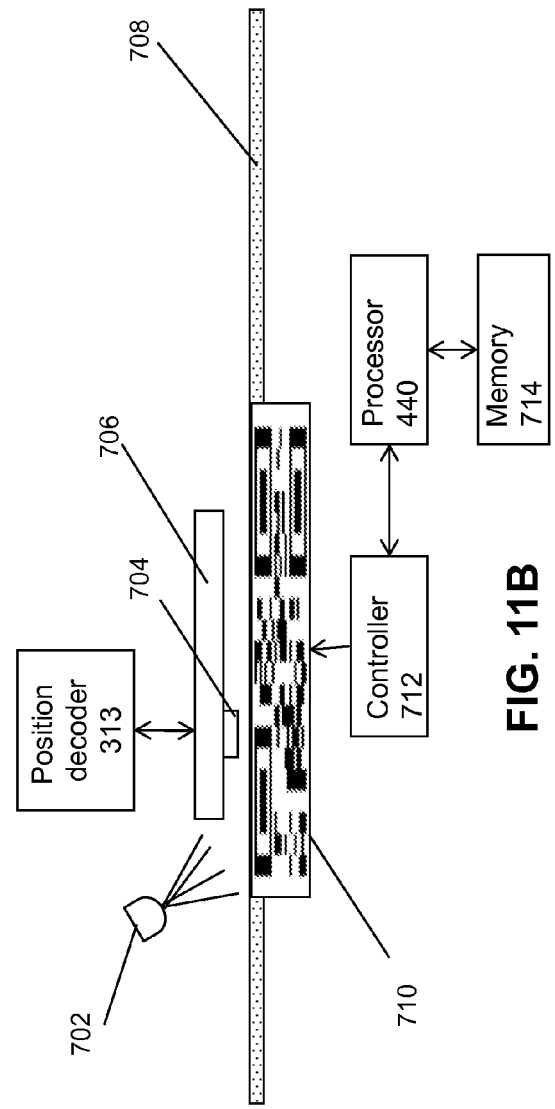

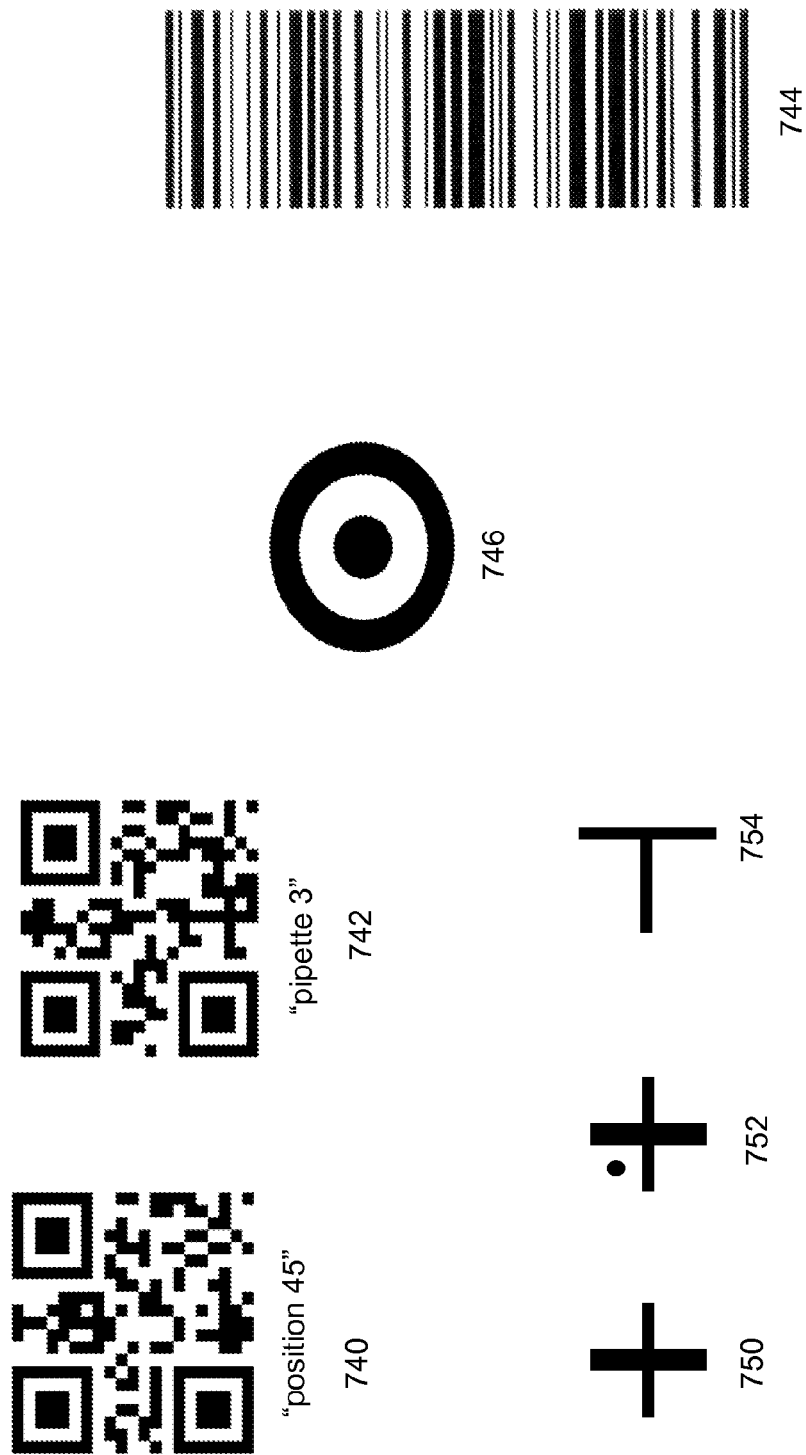

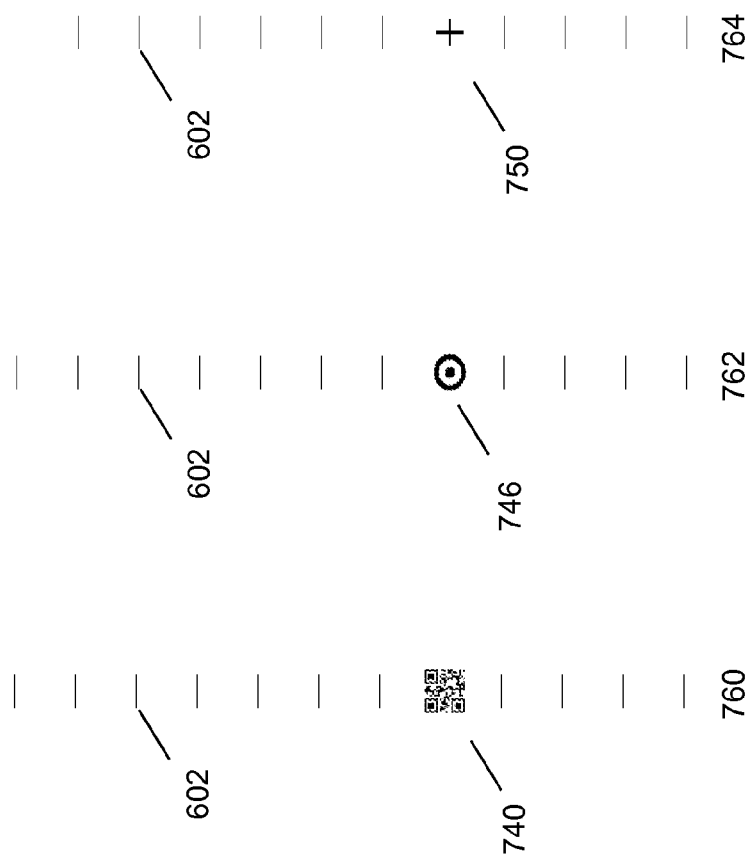

NON-CONTACT OPTICAL ENCODING SCHEME FOR INTELLIGENT AUTOMATION PUCK

CROSS-REFERENCE TO RELATED APPLICATIONS

This application claims priority to U.S. provisional application Ser. No. 61/651,296 filed May 24, 2012, which is incorporated herein by reference in its entirety.

TECHNOLOGY FIELD

The present invention relates in general to an automation system for use in a laboratory environment and, more particularly, to systems and methods for transporting patient samples for in vitro diagnostics (IVD) in a clinical analyzer via active transport devices. Embodiments of the present invention are particularly well suited for, but in no way limited to, optical encoding for conveying local position information to independent carriers having active direction and routing capabilities.

BACKGROUND

In vitro diagnostics (IVD) allows labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials containing patient samples have been loaded. The analyzer extracts a liquid sample from the vial and combines the sample with various reagents in special reaction cuvettes or tubes (referred to generally as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer), which may include immunoassay (IA) and clinical chemistry (CC) stations. Some traditional IVD automation track systems comprise systems that are designed to transport samples from one fully independent module to another standalone module. This allows different types of tests to be specialized in two different stations or allows two redundant stations to be linked to increase the volume of sample throughput available. These lab automation systems, however, are often bottlenecks in multi-station analyzers. Relatively speaking, traditional lab automation systems lack large degrees of intelligence or autonomy to allow samples to independently move between stations.

In an exemplary prior art system, a friction track, much like a conveyor belt, shuttles individual carrier mechanisms, sometimes called pucks, or racks of containers between different stations. Samples may be stored in sample containers, such as test tubes that are placed into a puck by an operator or robot arm for transport between stations in an analyzer along the track. This friction track, however, can only move in one direction at a time and any samples on the track will move in the same direction at the same speed. When a sample needs to exit the friction track, gating/switching can be used to move individual pucks into offshoot paths (sometimes called sidecars or pullouts). A drawback with this set-up is that singulation, which is often slow, must be used to control the direction of any given puck at each gate and switch. For example, if two pucks are near one another and only one puck should be redirected into an offshoot path, it becomes difficult to control a switch so that only one puck is moved into the offshoot path and ensure that the proper puck is pulled from the friction track. This has created the need in many prior art systems to have pucks stop at a gate so that individual pucks can be released and switched one at a time at each decision point on a track.

Another way that singulation has been used in friction track-based systems is to stop the puck at a gate and allow a barcode reader to read a barcode on the sample tube. Because barcode readers are slow relative to the amount of time needed to switch a puck between tracks, scanning introduces hard singulations into the flow on a track and causes all nearby pucks to halt while a switching determination is made. After a determination is made, singulation may be further used to ensure that only the scanned puck proceeds by using a physical blockage to prevent the puck behind the scanned puck from proceeding while the scanned puck is switched.

U.S. Pat. No. 6,202,829 shows an exemplary prior art friction track system that includes actuated mechanical diversion gates that can be used to direct pucks off of the main track onto sidecar tracks. As explained therein, the diversion process can require multiple mechanical gates to singulate and separate individual pucks, stopping each puck multiple times and allowing each puck to be rotated so that a barcode can be read before a diversion decision is made. Such a system increases latency and virtually ensures that each time a diversion gate is added to a friction track the gate adds another traffic bottleneck. Such a system results in natural queuing at each diversion gate, further increasing the amount of time that each sample spends on the friction track.

While there has been some development of autonomous transport carriers outside the IVD environment, such as industrial and shipping environments, there has yet to be an effective system that uses independently routable and positionable carriers in an IVD setting. One reason for the lack of automated carriers may include the need for precise positioning of vessels holding samples or reagents in relation to stations, such as testing stations or other sample handling stations. For example, a carrier must be able to reliably position itself at a destination to within about a millimeter to allow aspiration of the sample carried. Similarly, the small size needed for carriers in an IVD setting and relatively small size of features of tracks used to transport samples present challenges in adapting systems and techniques used in industrial systems. Accordingly, there is a need for conveying reliable position information to carriers in an IVD setting.

SUMMARY

Embodiments of the present invention may address and overcome one or more of the above shortcomings and drawbacks by providing devices, systems, and methods for providing location information and trajectory information for use by intelligent carriers that transport samples. This technology is particularly well-suited for, but by no means limited to transport mechanisms in an automation system for use in an in vitro diagnostics (IVD) environment.

Embodiments of the present invention are directed to an automation system for use with an automated clinical chemistry analyzer and include a track having a first surface with one or more marks that indicate absolute position information on the first surface. The automation system also includes at least one independently movable carrier configured to move along the first surface and observe the relative motion of the first surface to determine a trajectory of the carrier.

According to one aspect of the invention, the marks on the track surface include at least one QR code, barcode, or at least one two-dimensional mark. According to another aspect, the two-dimensional mark is asymmetric. In another aspect, the independently movable carriers are configured to illuminate the first surface, observe successive images of the first surface, and compare successive images to determine a direction and/or a magnitude of the relative motion. In still another aspect, the independently movable carriers include a light source, an image sensor, and at least one processor configured to detect relative motion within a plurality of successive images captured by the image sensor.

According to another aspect of the invention, a track surface has a plurality of synchronization marks and each independently movable carrier is configured to use the plurality of synchronization marks to correct errors in the determined trajectory information. According to another aspect, the one or more marks comprise one or more static images on the first surface.

Another embodiment of the invention is directed to a carrier configured to travel along a track having a first surface for use with an automated clinical chemistry analyzer. The carrier includes a light source configured to illuminate the first surface, an image sensor for capturing images of the first surface illuminated by the light from the light source, and at least one processor configured to detect a relative motion by comparing a plurality of successive images captured by the image sensor, wherein the relative motion corresponds to a trajectory of the carrier.

According to yet another aspect of the invention, a carrier is configured to adjust the trajectory in response to the relative motion. According to another aspect of the invention, a carrier is configured to observe one or more marks on the first surface to determine an absolute position along the track. In another aspect, the carrier is configured to obtain non-positional data from the marks on the first surface. In still another aspect, the carrier is configured to utilize the relative motion to determine a substantially real-time position of the carrier along the track. In yet another aspect, the carrier is configured to observe one or more synchronization marks on the first surface of the track. Furthermore, in another aspect, the carrier is configured to utilize the synchronization marks to adjust the determination of the substantially real-time position of the carrier. According to a further aspect, the carrier is configured to follow a visible line on the first surface of the track.

Another embodiment of the invention is directed to a method for transporting items in an IVD environment, whereby a first surface of a track along which one or more independently movable carriers (that hold one or more fluid samples) move is illuminated. Successive images of the first surface are observed using an imaging sensor, and compared using at least one processor, to determine at least one of a direction and a magnitude of the relative motion of the carriers. The method further determines an absolute position of at least one of the carriers by detecting one or more reference marks on the track surface. According to one aspect of the invention, the items transported include fluid samples or reagents.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures:

FIGS. 2A and 2B are diagrammatic views of track geometries that can be used with the automation system embodiments disclosed herein;

FIG. 4A is a perspective view of an exemplary carrier that can be used with the embodiments disclosed herein;

FIGS. 10A and 10B are top views of exemplary track sections employing dynamic marks for routing carriers in certain embodiments;

FIGS. 11A and 11B are diagrammatic side views of an image sensor of a carrier interacting with a track surface in certain embodiments;

FIG. 14 is a depiction of exemplary types of absolute position marks for use with certain embodiments;

FIG. 15 depicts absolute position marks in the context of synchronization marks for use with certain embodiments;

DETAILED DESCRIPTION OF ILLUSTRATIVE EMBODIMENTS

Figure 1:
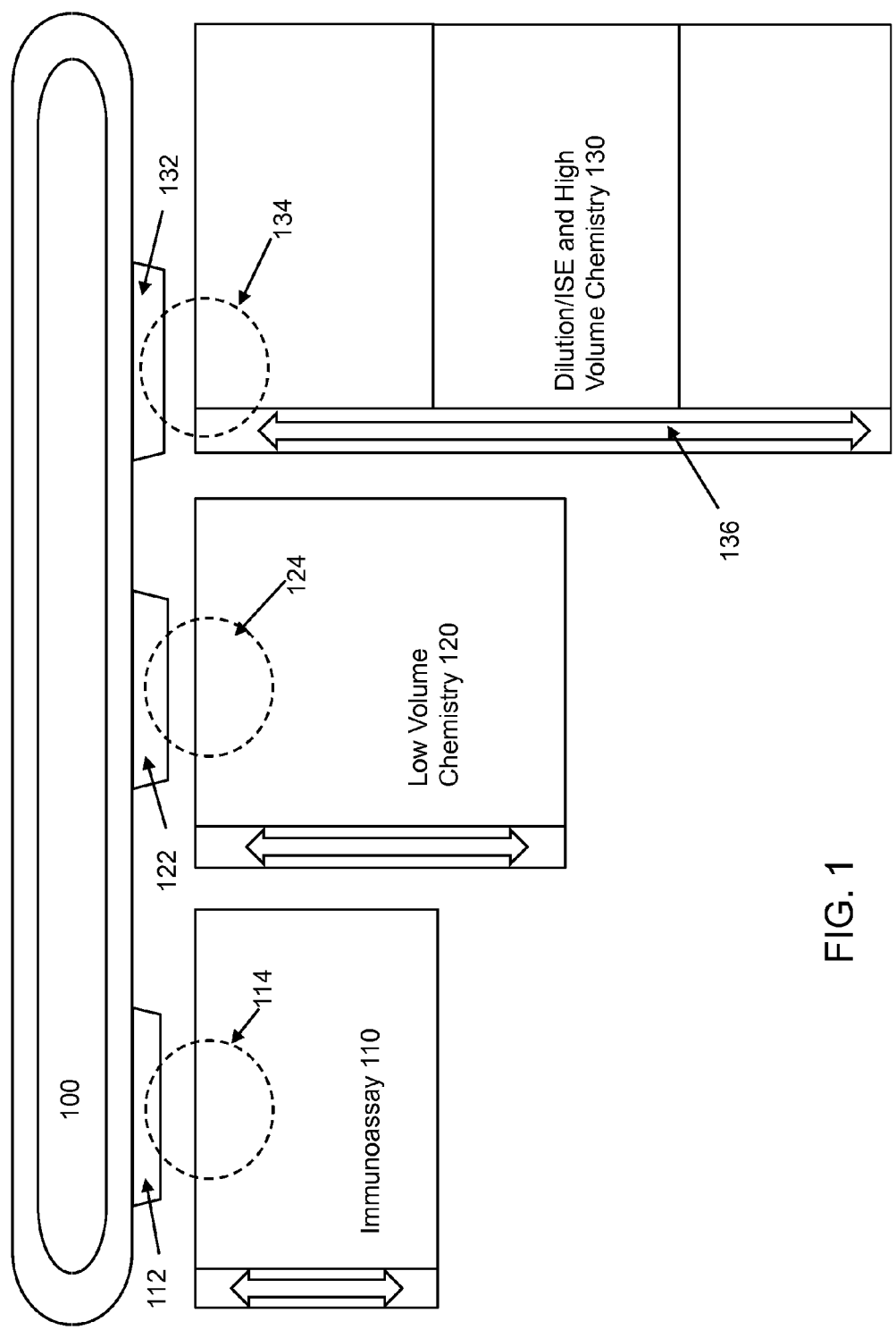
FIG. 1 is a top view of an exemplary clinical chemistry analyzer geometry that can be improved by use of the automation system embodiments disclosed.

Terms and Concepts Associated with Some Embodiments

Analyzer: Automated clinical analyzers ("analyzers") include clinical chemistry analyzers, automated immunoassay analyzers, or any other type of in vitro diagnostics (IVD) testing analyzers. Generally, an analyzer performs a series of automated IVD tests on a plurality of patient samples. Patient samples may be loaded into an analyzer (manually or via an automation system), which can then perform one or more immunoassays, chemistry tests, or other observable tests on each sample. The term analyzer may refer to, but is not limited to, an analyzer that is configured as a modular analytical system. A modular analytical system includes an integrated and extendable system comprising any combinations of a plurality of modules (which can include the same type of module or different types of modules) interconnected in a linear or other geometric configuration by an automation surface, such as an automation track. In some embodiments, the automation track may be configured as an integral conveyance system on which independent carriers are used to move patient samples and other types of material between the modules. Generally, at least one module in a modular analytical system is an analyzer module. Modules may be specialized or made redundant to allow higher throughput of analytical tasks on patient samples.

Analyzer module: An analyzer module is a module within a modular analyzer that is configured to perform IVD tests, such as immunoassays, chemistry tests, or other observable tests on patient samples. Typically, an analyzer module extracts a liquid sample from a sample vessel and combines the sample with reagents in reaction cuvettes or tubes (referred to generally as reaction vessels). Tests available in an analyzer module may include, but are not limited to, a subset of electrolyte, renal or liver function, metabolic, cardiac, mineral, blood disorder, drug, immunoassay, or other tests. In some systems, analyzer modules may be specialized or made redundant to allow higher throughput. The functions of an analyzer module may also be performed by standalone analyzers that do not utilize a modular approach.

Carrier: A carrier is a transportation unit that can be used to move sample vessels (and, by extension, fluid samples) or other items in an automation system. In some embodiments, carriers may be simple, like traditional automation pucks (e.g., passive devices comprising a holder for engaging a tube or item, a friction surface to allow an external conveyor belt in the automation track to provide motive force, and a plurality of sides that allow the puck to be guided by walls or rails in the automation track to allow the track to route a puck to its destination). In some embodiments, carriers may include active components, such as processors, motion systems, guidance systems, sensors, and the like. In some embodiments, carriers can include onboard intelligence that allows carriers to be self-guided between points in an automation system. In some embodiments, carriers can include onboard components that provide motive forces while, in others, motive forces may be provided by an automation surface, such as a track. In some embodiments, carriers move along automation tracks that restrict motion to a single direction (e.g., fore and aft) between decision points. Carriers may be specialized to a given payload in an IVD environment, such as having a tube holder to engage and carry a sample tube, or may include mounting surfaces suitable to carry different items around an automation system. Carriers can be configured to include one or more slots (e.g., a carrier may hold one or a plurality of sample vessels).

Central controller or processor: A central controller/processor (which may sometimes be referred to as a central scheduler) is a processor that is part of the automation system, separate from any processors onboard carriers. A central controller can facilitate traffic direction, scheduling, and task management for carriers. In some embodiments, a central controller can communicate with subsystems in the automation system and wirelessly communicate with carriers. This may also include sending trajectory or navigational information or instructions to carriers and determining which carriers should go where and when. In some embodiments, local processors may be responsible for managing carriers on local track sections, such as managing local queues. These local processors may act as local equivalents to central controllers.

Decision point: Decision points are points on an automation track where different navigational or trajectory decisions may be made for different carriers. A common example includes a fork in a track. One carrier may proceed without turning, while another may slow down and turn. Decision points may include stopping points at instruments, where some carriers may stop, while others may proceed. In some embodiments, deceleration zones ahead of turns may act as decision points, allowing carriers that will be turning to slow down to limit lateral forces, while others may proceed if not turning or if the motion profile for that carrier does not require slowing down. The decisions made at decision points can be made by processors onboard carriers, processors local to the track section, a central processor, or any combination thereof, depending on the embodiment.

Independent carrier: In some embodiments, carriers may be characterized as independently controlled carriers. Independently controlled carriers are carriers with independently controlled trajectories. In some embodiments, independent carriers may be operating at the same time, on the same track, with carriers carrying one or a plurality of combinations of payloads that differ by size, weight, form factor, and/or content. The trajectories of each independently controlled carrier may be limited by a motion profile that includes; maximum jerk, acceleration, direction, and/or speed for the carrier while moving in the automation system. The motion profile can limit or define the trajectory for each carrier independently. In some embodiments, a motion profile can be different for different sections of the automation system (e.g., in straight track sections vs. around curves to account for the added lateral forces while turning), for different carrier states (e.g., an empty carrier may have a different motion profile from a carrier transporting a sample or from a carrier transporting a reagent or other item), and/or for different carriers. In some embodiments, carriers can include onboard propulsion components that allow individual carriers to independently operate responsive to a motion profile or trajectory or destination instructions intended for each separate carrier.

Intelligent carrier/semi-autonomous carriers: In some embodiments, carriers may be characterized as intelligent carriers. An intelligent carrier is a carrier with onboard circuits that participates in motion, routing, or trajectory decisions. An intelligent carrier can include digital processors that execute software instructions to proceed along an automation surface responsive to the instructions or onboard analog circuits that respond to motion input (e.g., line follower circuits). Instructions may include instructions characterizing motion profiles, traffic, or trajectory rules. Some intelligent carriers may also include onboard sensors to assist onboard processors to route the carrier or make decisions responsive to the carrier's environment. Some intelligent carriers may include onboard components, such as motors or magnets, which allow the carrier to move responsive to control of an onboard processor.

In vitro diagnostics (IVD): In vitro diagnostics (IVD) are tests that can detect diseases, conditions, infections, metabolic markers, or quantify various constituents of bodily materials/fluids. These tests are performed in laboratory, hospital, physician office, or other health professional settings, outside the body of a patient. IVD testing generally utilizes medical devices intended to perform diagnoses from assays in a test tube or other sample vessel or, more generally, in a controlled environment outside a living organism. WD includes testing and diagnosis of disease or quantifying various constituents of bodily materials/fluids based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with analyzers into which tubes or vials containing patient samples have been loaded. IVD can refer to any subset of the IVD functionality described herein.

Landmarks: In embodiments where carriers include onboard sensors, optical or other marks in track surfaces or locations viewable/sensible from track surfaces can act as landmarks. Landmarks can convey geographic information to carriers, such as a current location, upcoming stopping location, decision point, turn, acceleration/deceleration points, and the like.

Lab automation system: Lab automation systems include any systems that can automatically (e.g., at the request of an operator or software) shuttle sample vessels or other items within a laboratory environment. With respect to analyzers, an automation system may automatically move vessels or other items to, from, amongst, or between stations in an analyzer. These stations may include, but are not limited to, modular testing stations (e.g., a unit that can specialize in certain types of assays or can otherwise provide testing services to the larger analyzer), sample handling stations, storage stations, or work cells.

Module: A module performs specific task(s) or function(s) within a modular analytical system. Examples of modules may include: a pre-analytic module, which prepares a sample for analytic testing, (e.g., a decapper module, which removes a cap on top of a sample test tube); an analyzer module, which extracts a portion of a sample and performs tests or assays; a post-analytic module, which prepares a sample for storage after analytic testing (e.g., a recapper module, which reseals a sample test tube); or a sample handling module. The function of a sample handling module may include managing sample containers/vessels for the purposes of inventory management, sorting, moving them onto or off of an automation track (which may include an integral conveyance system, moving sample containers/vessels onto or off of a separate laboratory automation track, and moving sample containers/vessels into or out of trays, racks, carriers, pucks, and/or storage locations.

Payload: While exemplary carriers are described with respect to carrying patient samples, in some embodiments, carriers can be used to transport any other reasonable payload across an automation system. This may include fluids, fluid containers, reagents, waste, disposable items, parts, or any other suitable payloads.

Processor: A processor may refer to one or more processors and/or related software and processing circuits. This may include single or multicore processors, single or multiple processors, embedded systems, or distributed processing architectures, as appropriate, for implementing the recited processing function in each embodiment.

Pullouts, sidecars, offshoot paths: These terms may be used to refer to track sections that are off the main portion of a track system. Pullouts or sidecars may include chords, parallel tracks, or other suitable means for separating some carriers from a primary traffic pattern. Pullouts or sidecars may be configured to facilitate physical queues or allow certain carriers to stop or slow down without disrupting traffic on a main track section.

Samples: Samples refers to fluid or other samples taken from a patient (human or animal) and may include blood, urine, hematocrit, amniotic fluid, or any other fluid suitable for performing assays or tests upon. Samples may sometimes refer to calibration fluids or other fluids used to assist an analyzer in processing other patient samples.

STAT (short turnaround time) sample: Samples may have different priority assigned by a laboratory information system (LIS) or operator to assign STAT priority to samples that should take precedent over non-STAT samples in the analyzer. When used judiciously, this may allow certain samples to move through the testing process faster than other samples, allowing physicians or other practitioners to receive testing results quickly.

Station: A station includes a portion of a module that performs a specific task within a module. For example, the pipetting station associated with an analyzer module may be used to pipette sample fluid out of sample containers/vessels being carried by carriers on an integrated conveyance system or a laboratory automation system. Each module can include one or more stations that add functionality to a module.

Station/module: A station includes a portion of an analyzer that performs a specific task within an analyzer. For example, a capper/decapper station may remove and replace caps from sample vessels; a testing station can extract a portion of a sample and perform tests or assays; a sample handling station can manage sample vessels, moving them onto or off of an automation track, and moving sample vessels into or out of storage locations or trays. Stations may be modular, allowing stations to be added to a larger analyzer. Each module can include one or more stations that add functionality to an analyzer, which may be comprised of one or more modules. In some embodiments, modules may include portions of, or be separate from, an automation system that may link a plurality of modules and/or stations. Stations may include one or more instruments for performing a specific task (e.g., a pipette is an instrument that may be used at an immunoassay station to interact with samples on an automation track). Except where noted otherwise, the concepts of module and station may be referred to interchangeably.

Tubes/sample vessels/fluid containers: Samples may be carried in vessels, such as test tubes or other suitable vessels, to allow carriers to transport samples without contaminating the carrier surfaces.

Exemplary Embodiments

The above problems in the prior art have motivated the discovery of improved apparatus and methods for reliably and/or automatically transporting samples between stations/testing modules within an automated clinical analyzer (analyzer). Specifically, by providing encoded distance or position marks on a track surface, semi-autonomous, independently movable carriers having imaging devices can be used to reliably transport samples, such as, for example, patient fluid samples in an in vitro diagnostics (IVD) clinical analyzer. These carriers can be configured to transport samples substantially faster than prior methods, allowing reliable scheduling of tests, a reduction of traffic in the automation system, and reduced latency and reliable throughput of tests within the analyzer. Some embodiments exploit the semi-autonomy of the sample carriers to provide transit between stations in less than a single operation cycle, effectively removing or greatly reducing automation of sample placement as a performance bottleneck, and allowing more flexible sample scheduling options. The rapid motion can create difficulty in reckoning the position of a carrier with sufficient accuracy in an IVD environment. By providing marks on a track surface, a carrier can determine a reference position when passing a position mark and then observe the relative motion of a surface of the track to determine its current real-time position within the track. Additional synchronization marks can be provided on the track surface to calibrate the real-time positioning and trajectory and prevent positioning or trajectory errors from accumulating between reference position marks. Marks may be provided on a track by providing marks on, in, within, or along a surface as described herein.

Embodiments of the present invention include systems and methods that provide a more efficient lab automation system to allow samples to be shuttled between and amongst various analyzer stations, including testing stations and sample handling stations, with less latency and more individual control. Embodiments of the present invention can reduce or eliminate queues experienced by samples traversing the automation system. Usually, samples need to undergo many different types of testing in an automated chemical analyzer, which may not be available in a single testing station. Testing stations within an analyzer can be adapted for specialized testing. For example, immunoassays may be performed by an immunoassay station that includes certain incubation capabilities and uses specific reagents that are unique to immunoassays. Chemical analysis can be performed by a chemical analyzer and electrolyte chemistry analysis can be conducted by an ion-selective electrode (ISE) clinical analyzer. By using this modular approach, an analyzer can be adapted not only to the types of testing being done on samples, but also the frequency and volume of testing necessary to accommodate the needs of the lab. If additional immunoassay capability is needed, a lab may choose to add additional immunoassay stations and increase overall throughput for immunoassay testing in their system. Stations can also include pre-analytic stations or post-analytic stations. For example, a sample handling station may act as a pre-analytic station that decaps, mixes, verifies quality, or otherwise prepares a sample for analytic testing stations. A post-analytic station can include similar stations that sort and prepare a sample to be stored. It should be appreciated that the automation systems described herein may be suitable for transport within and amongst any of the available stations within the analyzer or throughout the IVD environment.

An exemplary track geometry, for use in transporting samples within an analyzer typical in prior art configurations, is shown in FIG. 1. This track can include prior art friction tracks, which may introduce challenges in designing a track system. However, certain embodiments of the present invention could also use a similar geometry without necessarily employing a friction track for motion. Track 100 can be a generally oval-shaped track that conveys samples in pucks or trays between various stations, such as sample preparation or analyzing/testing stations 110, 120, and 130. Track 100 could be a single direction track or, in some instances, a linear bidirectional track. In this exemplary set-up, each analyzer 110, 120, and 130 is serviced by a respective sidecar 112, 122, 132. At the junction between the track 100 and each sidecar, a gate or switch can be placed that allows samples to be diverted to or from track 100 to the sidecar. The oval nature of track 100 can be used to circulate samples while they wait for access to each analyzer. For example, analyzer 110 may have a full queue in sidecar 112, such that new samples on track 100 cannot be diverted to sidecar 112 until analyzer 110 finishes handling a pending sample in sidecar 112 and inserts it back into the main traffic flow of track 100.

In some prior art systems, each sidecar can be serviced by a handling mechanism such as sample probe arms 114, 124, and 134. These robotic handling arms can aspirate sample material from samples in a sidecar via a probe needle, or can pick up a sample tube from the sidecar and transport it into the corresponding testing station. In this exemplary system, the available testing stations include an immunoassay station 110, a low-volume chemistry station 120, and an expandable dilution/ISE electrolyte and high-volume chemistry station (or stations) 130. Some advantages of this approach are that the track 100 can be part of a separate lab automation system that can be added onto otherwise self-contained stations, and the track 100 and stations 110, 120, and 130 can be independently upgraded, purchased, or serviced. Some stations, such as high-volume chemistry station 130, can include their own friction track 136 that operates independently of track 100. Friction track 136 can include a bidirectional friction track that allows samples to move between sub-modules of high-volume chemistry station 130. A drawback of this type of system is that the separate friction tracks operate independently and, thus, control of overall automation becomes more complicated. Furthermore, transitions between friction tracks 136 and 100 can be slow and cumbersome, particularly where there is no direct route between two friction tracks. In some systems, moving between tracks may require lifting and placing samples via a robot arm.

Prior art lab automation systems for analyzers generally treat individual analyzer testing stations as generic destinations for a sample on the track. In some embodiments of the present invention, the lab automation system can be integrated within the individual testing stations, which can substantially reduce or eliminate the complexity of the individual testing stations and reduce the need for separate sample handling systems within each station. In some embodiments, by integrating the lab automation system into the stations, the system can begin to treat individual stations less as generic destinations and more as portions of a multi-route track onto which a sample can travel.

FIG. 2A shows one embodiment of a track system that can be adapted for use with the present invention. Track 150 is a rectangular/oval/circular track on which sample carriers move in a clockwise (or counterclockwise) direction. Track 150 may be unidirectional or bidirectional. Carriers can transport any suitable payload within an IVD environment, such as fluid samples, reagents, or waste. Fluids, such as patient samples, can be placed in a container or vessel, such as a test tube, vial, cuvette, etc. that can be transported by a carrier. Carrier and, by extension, payloads such as samples, can move on the main track 150 or be diverted via decision points such as 164 or 166. These decision points can be mechanical gates (as in the prior art) or other mechanisms suitable for allowing a sample to be diverted from the main track 150 to a sidecar, such as 160, 160A, 160B, and 160C as described herein. By way of example, if a sample carrier is traversing the main path 150 and reaches decision point 166, it can be made to continue on the main track to segment 162 or it can be made to divert to sidecar 160. The systems and methods by which the decision can be made to divert the sample at decision point 166 are described throughout.

FIG. 2B shows an alternative track layout that may be suitable for certain embodiments of the present invention. Track 170 is also a generally circular track with sample carriers moving clockwise (or counterclockwise). In this example, rather than having sidecars outside of the track, pullouts 180, 180A, and 180B are chords within the track. Similarly, when sample carriers reach decision points, they may be diverted off of the main path to a side path such as path 180. At decision point 186, a sample on the main track 170 can be made to continue on the main track portion 172 or be diverted onto path 180. Once an analyzer station along handling path 180 is done processing the sample, the sample proceeds to decision point 184 where it may be placed back onto the main path 170.

Figure 3:
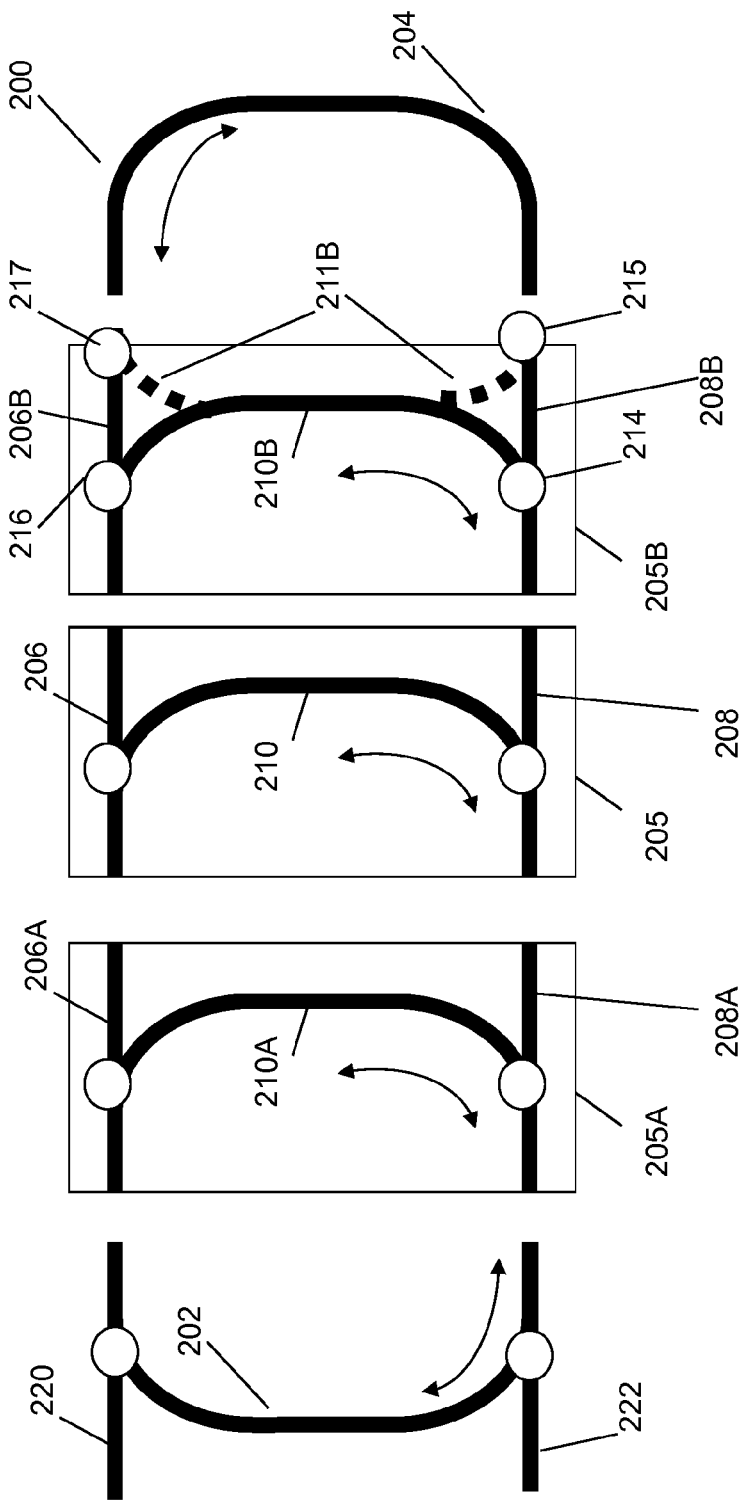
FIG. 3 is a diagrammatic view of an exemplary modular track configuration that can be used with the embodiments disclosed herein.

FIG. 3 shows a modular approach to the automation system track that can be used for certain embodiments of the present invention. In this example, the tracks may be integrated into individual analyzer stations, such that the track can be used as part of the internal motion or sample handling system of individual lab stations. In the prior art, it is common to have multiple different types of motion systems within different analyzer/testing stations. For example, some stations can include friction tracks for shuttling pucks or trays of sample tubes, and may include carousels containing smaller vessels, such as cuvettes and reaction vessels, into which portions of the sample can be aspirated and dispensed. In some embodiments, by integrating portions of the track system into the analyzer stations themselves, each station can include its own queuing logic and may be simplified to eliminate unnecessary internal motion systems.

With respect to FIG. 3, the track 200 can be broken into modular components that are integrated into analyzer modules. In this exemplary track, modules 205, 205A, and 205B can be combined with one another and optionally other modular track components 202 and 204 to form a track similar to that shown in FIG. 2B. For instance, 205A can be a module that performs the same function as immunoassay 110 (FIG. 1), 205 can be a module that performs the same function as low-volume chemistry module 120 (FIG. 1), and 205B can be a module that performs ISE electrolyte testing, like module 130 (FIG. 1). In this example, the main outer track can be formed by track segments 202, 204, 206, 206A, 206B, 208, 208A, and 208B. Within the analyzer modules 205, 205A, and 205B, internal paths 210, 210A, and 210B, form pullout from the main track. The internal paths can be used for internal queuing and can be managed independently within each analyzer module to allow each module to have greater control over samples to be processed.

One advantage of integrating track 200 and sub-paths 210, 210A, and 210B into the analyzer modules 205, 205A, and 205B, respectively, is that the internal handling mechanisms within each analyzer module can be specially adapted to better coordinate with the track sub-paths. In some embodiments, modules 205, 205A, and 205B can be adapted to process each sample within a period that is less than an operation cycle of the overall analyzer, leaving enough time for the sample to be routed along the track system to another module after processing and allowing the other module to immediately process the sample on the next operation cycle. As used herein, an operation cycle is a unit of time used by scheduling algorithms to allot processing time to modules for sample assays. These can be dynamic or fixed and can allow synchronous operation of the modules in the analyzer and provide a reliable timing model for scheduling samples amongst multiple modules in the analyzer. The operation cycle time can be chosen to be the time needed by any given module between when it starts processing a first sample, and when it is ready to process another sample under expected steady-state conditions. For example, if an analyzer can process one test every three seconds, and the expected average tests per sample is seven, the operation cycle time can be 21 seconds. It should be understood that individual modules can implement efficiency techniques, such as parallelism or processing multiple samples within a cycle, to maximize throughput, even when the number of tests-per-sample varies from an expected amount. Furthermore, it should be understood that in some embodiments, individual modules have different operation cycle times, and these modules can operate substantially asynchronously from one another. Virtual queues or buffers can be used to assist the management of sample scheduling where cycle times or demand vary between modules.

Enabling transit between modules in the analyzer in a reliable time frame, on the order of a single operation cycle or less, achieves many performance advantages not possible with prior art track systems. If a sample can be reliably handled by an analyzer module and transported to the next analyzer module within a single cycle of the analyzer, traffic handling in queuing becomes much simpler, throughput becomes more consistent, and latency can be controlled and reduced. Essentially, in such an analyzer, a sample can reliably be handled by the track system and processed uniformly, such that a sample does not sit idly on the track system waiting in queues. Furthermore, queues within the system, such as queues within a given analyzer module, can reliably be shortened, limited by the number of modules within the system.

In some embodiments of the present invention, the reliable and rapid nature of the track system enables queues to be virtual, rather than physical. A virtual queue can be handled in software, rather than by physical limitations. Traditionally, queues have been physical. The simplest physical queue is effectively a traffic jam at any given part of a sample handling operation. A bottleneck creates a first-in first-out (FIFO) queue, where sample carriers are effectively stopped in a line, providing a buffer so that an analyzer or a decision point can request the next sample in the queue when it is ready. Most prior art lab automation tracks maintain FIFO processing queues to buffer samples that are waiting to be processed by the attached modules (analyzers or pre/post-analytic devices). These buffers allow the track to process sample tubes at a constant rate, even though the modules or operator requests can create bursts of demand. FIFO queues can also substantially increase the throughput of the individual modules by allowing them to perform preprocessing tasks for future samples, for example, prepare a cuvette or aspirate reagent, while processing the current sample. While the rigid predictability of FIFO queues enables the parallelization of some processing tasks, it also can prevent the modules from using opportunistic scheduling that may increase throughput by reordering tests on samples to optimize resources. For example, the internal resource conflicts of most immunoassay analyzers can be so complex that the analyzers need to interleave the tests from multiple samples in order to reach maximum efficiency. A FIFO queue can reduce the throughput of these analyzers by as much as 20%. Another challenge with FIFO queues is their inability to handle priority samples (e.g., a STAT sample). If a STAT sample needs to be processed immediately, the entire FIFO queue has to be flushed back onto the main track, delaying all other samples on the track and forcing the original module to slowly rebuild its queue.

Another type of queue is a random access (RA) queue. A carousel is an example of a physical RA queue found in analyzer modules. By aliquoting a portion of a sample into one or more vessels in a carousel ring, an analyzer module can select any of a number of samples to process at any time within the analyzer. However, carousels have many drawbacks, including added complexity, size, and cost. A carousel also increases the steady-state processing time, because a sample must be transferred into and out of the random-access queue. Processing delays depend on the implementation, such as the number of positions in a carousel. On the other hand, by having random access to samples, a local scheduling mechanism within a module can process samples in parallel, performing sub-steps in any order it desires.

In some embodiments, carousels or other RA queues can be eliminated from the modules and the sub-paths (e.g., 210) from the automation system can be used as part of an RA or FIFO queue. That is, if the travel time for a sample between any two points can be bounded to a known time that is similar to that of a carousel (such as predictably less than a portion of an operation cycle), the track 200 can be part of the queue for a given module. For example, rather than using a carousel, module 205 can utilize samples in carriers on sub-path 210. Preprocessing steps, such as reagent preparation, can be conducted prior to the arrival of a sample under test. Once that sample under test arrives, one or more portions of the sample can be aspirated into cuvettes or other reaction vessels for an assay. In some embodiments, these reaction vessels can be contained within module 205, off track, while in other embodiments, these reaction vessels can be placed in carriers on sub-path 210 to allow easy motion. If the sample under test is required to be at a module for longer than an operation cycle, or if multiple samples will be processed by the module during an operation cycle, the sub-path 210 can act as a queue for the module.

Furthermore, samples not yet under test, which may be currently located at other modules, can be scheduled for the next operation cycle. These next-cycle samples can be considered as residing in a virtual queue for module 205. A module can schedule samples to arrive during a given operation cycle for any sample on track 200. A central controller, or controllers associated with modules themselves, can resolve any conflicts over a sample for a given cycle. By giving a module prior knowledge of the arrival time of a sample, each module can prepare resources and interleave tests or portions of tests to more efficiently allot internal resources. In this manner, modules can operate on samples in a just-in-time manner, rather than using large physical buffers. The effect is that the virtual queue for a given module can be much larger than the physical capacity of the sub-path serving that module, and existing scheduling algorithms can be used. Effectively, each module can treat track 200 as it would treat a sample carousel in a prior art module.

It should also be appreciated that by employing virtual queues, in some embodiments, multiple modules can have multiple queues and can share a single queue or samples within a queue. For example, if two modules are equipped to perform a certain assay, a sample needing that assay can be assigned to a virtual queue for that assay, which is shared between the two modules capable of handling the assay. This allows load balancing between modules and can facilitate parallelism. In embodiments where reaction vessels are placed in carriers on track 200, an assay can be started at one module (e.g., reagents prepared and/or sample mixed in) and the assay can be completed at another (e.g., a reaction is observed at another module). Multiple modules can effectively be thought of as a multi-core processor for handling samples in some embodiments. In these embodiments, scheduling algorithms for the multiple modules should be coordinated to avoid conflicts for samples during a given operation cycle.

By employing virtual queues, modules can operate on samples while the samples are in the virtual queues of other modules. This allows low latency of samples, as each sample that is placed onto track 200 can be processed as quickly as the modules can complete the tests, without having to wait through a physical queue. This can greatly reduce the number of sample carriers on track 200 at any given time, allowing reliable throughput. By allowing modules to share queues or samples, load balancing can also be used to maximize throughput of the system.

Another advantage of using virtual queues is that STAT samples can be dynamically assigned priority. For example, a STAT sample can be moved to the head of any queue for the next operation cycle in software, rather than having to use a physical bypass to leapfrog a STAT sample to the head of a largely static physical queue. For example, if a module is expecting three samples to be delivered by track 200 for assays during the next operation cycle, a scheduler responsible for assigning samples to the module can simply replace one or more of the samples with the STAT sample, and have the track 200 deliver the STAT sample for processing during the next operation cycle.

If decision points such as 214 and 216 can be streamlined such that there is no need for a queue at each decision point, the only physical queues can be within sub-paths 210, 210A, and 210B. As described above, these can be treated as RA queues or FIFO queues. If a STAT sample is placed onto track 200, RA queues within sub-paths 210, 210A, and 210B need not be flushed, as the STAT sample can be processed immediately. Any FIFO queues can be individually flushed. For example, if a STAT sample is placed onto track 200 at section 222, the sample may be routed to the appropriate analyzer 205B via the outside track and decision point 216. If there are other samples (and, by extension, the sample carriers transporting those samples) waiting in the queue in path 210B, only those samples in the queue may need to be flushed to allow a STAT sample to take priority. If the outer track 200 is presumed to take less than an operation cycle to traverse, any samples that were flushed from the queue in 210B can simply be circulated around the track and placed immediately back into the queue in path 210B immediately behind the STAT sample, eliminating any down time caused by the STAT sample.

Entry paths 220 and 222 can be used to input samples to the track 200. For example, regular priority samples can be placed onto track 200 at input 220 and STAT priority samples can be placed on input 222. These inputs can be used as outputs for samples when complete, or other ports (not shown) can be used as the output paths for used samples. Input 220 can be implemented as an input buffer, acting as a FIFO queue for input samples seeking access to the track 200. Once a sample reaches the head of the queue at input 220, it can be moved onto the track (either by being placed in a carrier, or by being placed in a carrier when it is placed in input 220). A STAT sample can enter the track 200 immediately after being placed at input 222 or, if track 200 is overcrowded, the STAT sample can enter the track at the next available uncrowded operation cycle. Some embodiments monitor the number of carriers on the track during an operation cycle and limit the total number to a manageable amount, leaving the remainder in input queues. By restricting samples at the input, track 200 can be free of traffic, allowing it to always be operated in the most efficient manner possible. In these embodiments, the transit time of a sample between two modules can be a bounded value (e.g., less than some portion of an operation cycle), allowing simplified scheduling.

In some embodiments, the track system 200 can be designed to be bidirectional. This means that sample carriers can traverse the outside path and/or any sub-paths in either direction. In some embodiments, additional sub-paths, such as 211B accessed via additional decision points 215 and 217, can assist in providing bidirectional access. Bidirectional paths can have inherent advantages. For example, if normal priority samples are always handled in the same direction, a STAT sample can be handled in the opposite direction along the sub-path. This means that a STAT sample can essentially enter the exit of the sub-path and be immediately placed at the head of the queue without requiring the queue to be flushed. For example, if a STAT sample is placed on track 200 at segment 204, it can enter path 210B via decision point 214 and proceed into path 210B to be immediately placed at the head of any queue. Meanwhile, in all of these examples, because queues are presumed to be limited generally to sub-paths, there is no need to flush queues in other modules if a STAT sample does not need immediate access to those modules. Any additional modules that need to service a STAT sample on a subsequent cycle can flush their queues at that point, providing just-in-time access to a STAT sample without otherwise disrupting the operation of each analyzer module.

Modular design also allows certain other advantages. If the automation systems within an analyzer module are adapted to take advantage of the track system contained in the module, new features can be added that use the common track. For example, a module could have its own internal reagent carousel that includes all of the reagents necessary for performing the assays prescribed for the samples. When reagents stocked in the analyzer module run low, an operator can replenish the reagents in some embodiments by simply loading additional reagents onto carriers on the track 200. When the reagents on track 200 reach the appropriate module, the module can utilize mechanical systems, such as an arm or a feeder system that takes the reagents off of the track and places the reagents in the reagents store for the module.

In some embodiments, the individual track portions shown in FIG. 3, FIG. 2A, and FIG. 2B can be operated independently from one another, or can be passive. Independent carrier movement provides advantages over friction-based track systems, such as non-localized conveyor belts, where the entire friction track must be moved to effect movement of a sample carrier. This means that other samples also on that track must move at the same rate. This also means that if certain sections operate at different speeds, collisions between passive carriers carrying samples can occur.

FIG. 4A depicts an exemplary carrier 250 for use with the present invention. Carrier 250 can hold different payloads in different embodiments. One payload can be a sample tube 255, which contains a fluid sample 256, such as blood or urine. Other payloads may include racks of tubes or reagent cartridges, or any other suitable cartridge. Sample carrier 250 includes a main body 260, which can house the internal electronic components describe herein. The main body 260 supports a bracket 262, which can accept a payload. In some embodiments, this is a shallow hole that is designed to accept a fluid container 255 such as a sample tube, and hold it with a friction fit. In some embodiments, the friction fit can be made using an elastic bore or a clamp that can be fixed or energized with a spring to create a holding force. In some embodiments, sample racks and reagent cartridges can be designed to also attach to the bracket 262, allowing bracket 262 to act as a universal base for multiple payload types.

Body 260 can include or be coupled to guide portion 266, which allows the carrier 250 to follow a track between decision points. Guide portion 266 can include, for example, a slot to accept one or more rails in the track, providing lateral and/or vertical support. In some embodiments, the guide portion 266 allows the carrier 250 to be guided by walls in the track, such as the walls of a trough-shaped track. The guide portion 266 can also include drive mechanisms, such as friction wheels that allow a motor in the carrier body 260 to drive the carrier or puck 250 forward or backward on the track. The guide portion 266 can include other drive components suitable for use with the embodiments described throughout, such as magnets or induction coils. In some embodiments, the guide portion 266 can be physically constrained by the track, such that the range of motion is substantially bidirectional within the track and one-dimensional within the reference frame of the track (i.e., the motion is restricted transversely so that the carrier 250 can only move forward or backward along the track, even though the track may itself be two or three-dimensional). In some embodiments, the guide portion 266 can be less constrained laterally (e.g., more like a car on a road than a train on a track), such that the carrier 250 can control its lateral position, such as via a steering mechanism. In these embodiments, a carrier 250 can vary its position in two dimensions relative to the track. It will be appreciated that embodiments of two-dimensional position marks can be useful for facilitating the positioning of a carrier 250 in one or two dimensions.

Rewritable display 268 can be provided on the top of the carrier 250. This display can include an LCD oriented panel and can be updated in real time by the carrier 250 to display status information about sample 256. By providing the electronically rewritable display on the top of the carrier 250, the status information can be viewed at a glance by an operator. This can allow an operator to quickly determine which sample he/she is looking for when there are multiple carriers 250 in a group. By placing the rewritable display on top of the carrier 250, an operator can determine status information even when multiple carriers 250 are in a drawer or rack.

Figure 4B:
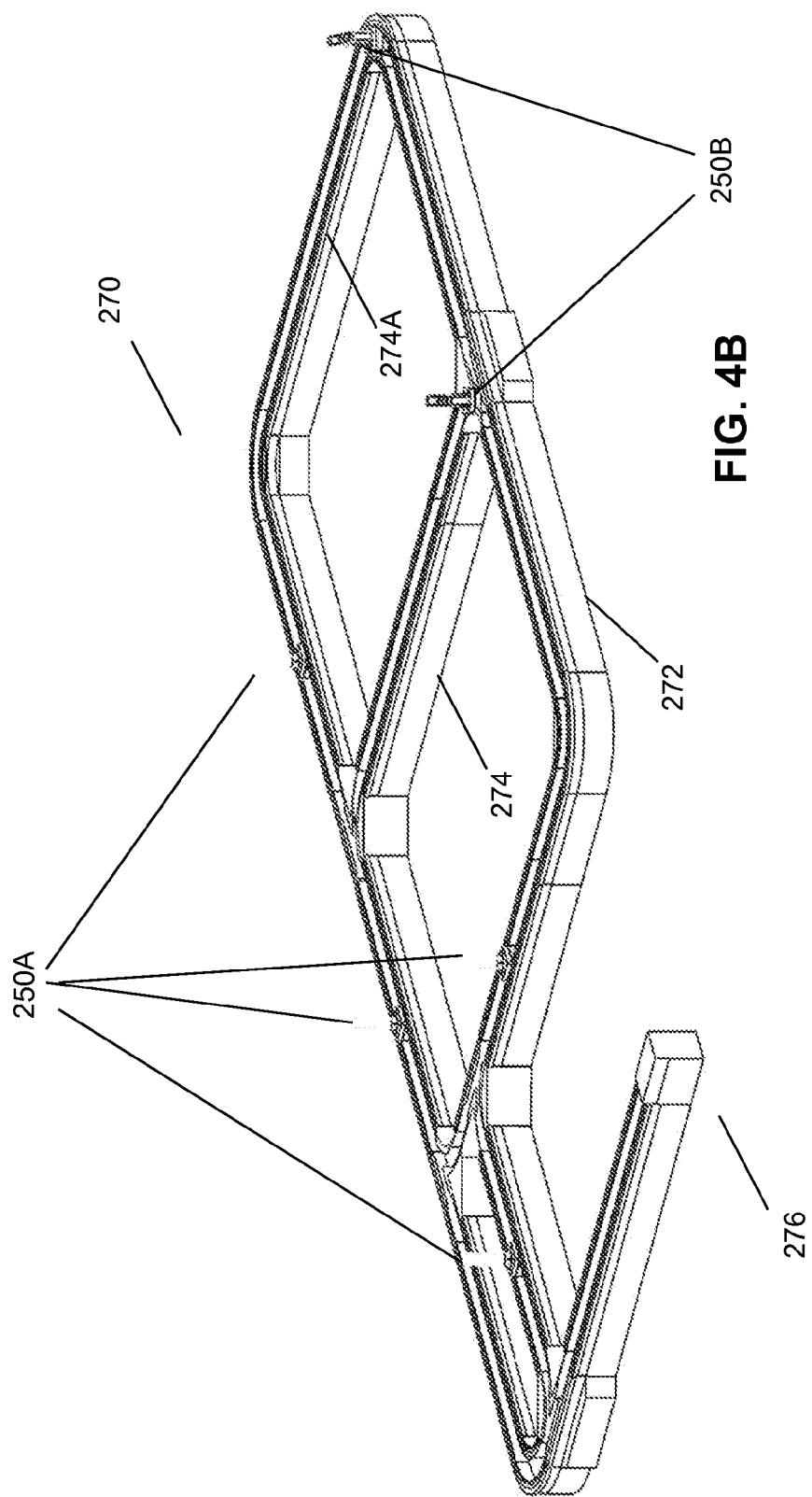
FIG. 4B is a perspective view of an exemplary track configuration that can be used with the embodiments disclosed herein.

FIG. 4B shows an exemplary track configuration 270 for use by carriers 250. In this example, carriers 250A transport sample tubes, while carriers 250B transport racks of tubes along main track 272 and/or sub-paths 274 and 274A. Path 276 can be used by an operator to place samples into carriers or remove samples from these carriers.

Figure 4C:
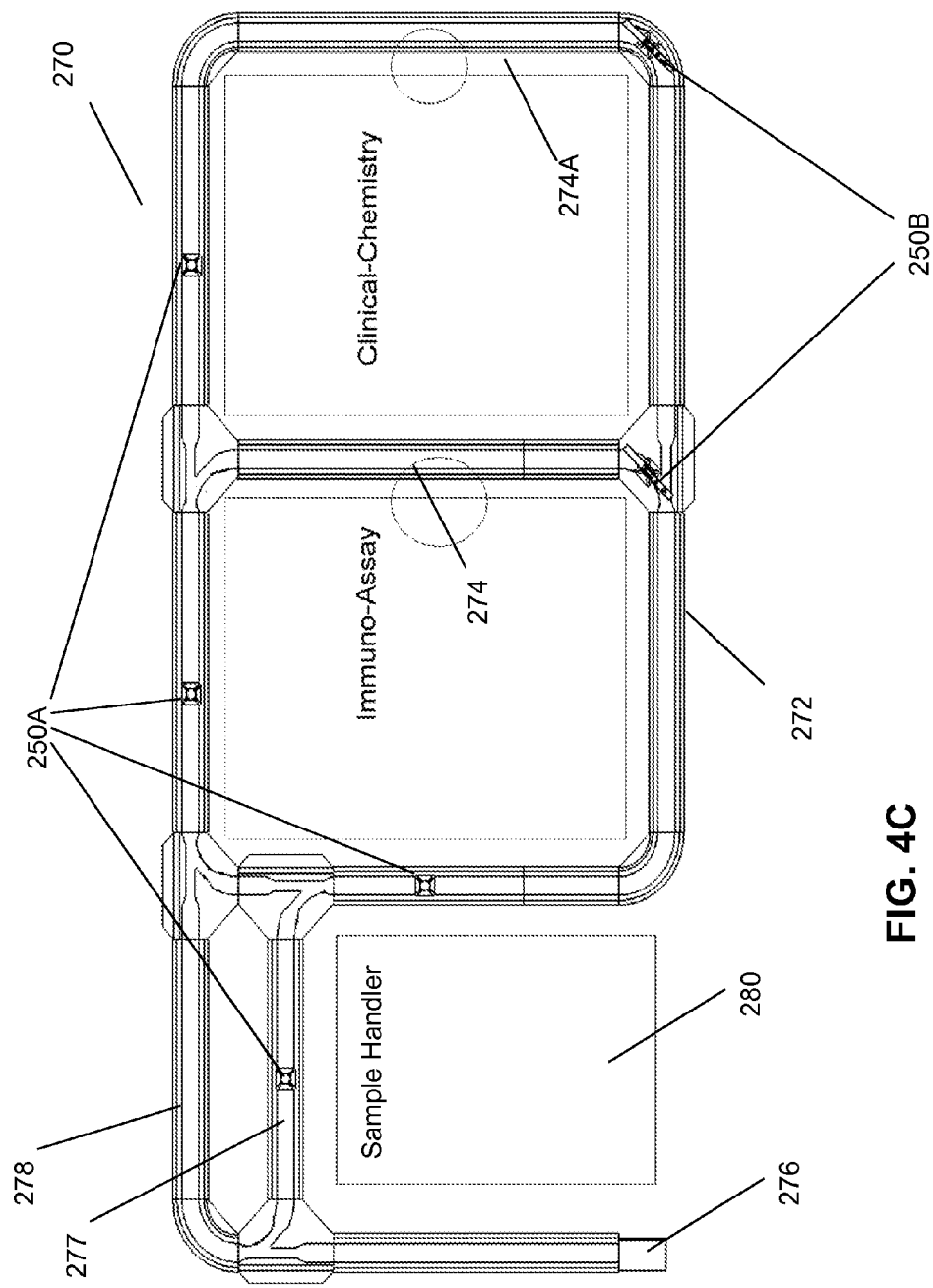
FIG. 4C is a top view of an exemplary track configuration that can be used with the embodiments disclosed herein.

FIG. 4C shows an additional view of an exemplary track configuration 270. In this example, sub-path 274 serves an immunoassay station, while sub-path 274A serves a clinical chemistry station. Input/output lane 276 can be served by a sample handler station 280 that uses sub-paths 277 and 278 to buffer samples for insertion or removal of the samples from the main track 272.

In some embodiments, the sample handler 280 can also load and unload samples or other payload to/from the carriers 250A and 250B. This allows the number of carriers to be reduced to the amount needed to support payloads that are currently being used by the stations in track system 270, rather than having a vast majority of carriers sitting idle on tracks 277 and 278 during peak demand for the analyzer. Instead, sample trays (without the carriers disclosed herein) can be placed/removed by an operator at input/output lane 276. This can reduce the overall cost of the system and the number of carriers needed can be determined by the throughput of the analyzer, rather than based on anticipating the peak demand for the analyzer in excess of throughput.

Intelligent Carriers

Whereas prior art lab automation systems utilize passive pucks or trays (e.g., the puck is a simple plastic or rubber brick that lacks active or autonomous systems, power, onboard processing, or control) to reduce cost and complexity, in some embodiments, the added complexity and cost necessary to integrate intelligence and autonomy into individual carriers (which can include intelligent pucks or trays in some embodiments) can provide benefits. Some embodiments can utilize intelligent independent carriers to enable certain improvements over passive pucks on friction-based tracks. For example, one disadvantage of prior art track systems is that, at each decision point, the decision for directing a puck is made by the track by rotating the puck and reading a barcode optically. Rotating and optical reading is a relatively slow process. Furthermore, this process can be redundant because the system has knowledge of the identification of the sample tube when the sample tube is placed into the puck by an operator. Embodiments of the present invention can include carriers that have means to identify the contents of the sample tube (and optionally communicate this information to the automation system) without requiring the carrier to be stopped, rotated, and read optically.

For example, a carrier can include an onboard optical reader to automatically read a barcode of a payload. The results of the scan can then be stored in the memory of a carrier if the carrier has onboard processing capability. Alternatively, an outside source, such as a hand barcode reader operated by an operator at the time of placing the sample into the carrier, can communicate the barcode information of the payload to the carrier via RF signal or other known means, such as communication protocol using temporary electrical contact or optical communication. In some embodiments, the association of the carrier with the payload can be stored external to the carrier and the identity of the carrier can be conveyed by the carrier to the system by RF, optical, or near-field communication, allowing the system to assist in routing or tracking the carrier and the payload. Routing decisions can then be made by the carrier or by identifying the carrier, rather than reading a unique barcode of a payload.

By moving processing capability and/or sensor capability onto each individual carrier, the carriers can participate actively and intelligently in their own routing through the track system. For example, if individual carriers can move independently of one another either by autonomous motive capabilities or by communication with the track, certain performance advantages can be realized.

By allowing carriers to move independently, carriers can move around the track faster. One limitation on the motion of a carrier is that it should not spill an open-tube sample. The limiting factor is generally not the velocity of the carrier in a straight line, but the acceleration and jerk experienced by the carrier (while speeding up, slowing down, or turning), which may cause splashing. For prior-art friction-based track systems, the velocity of the track is typically limited to prevent acceleration and jerk experienced by pucks from exceeding threshold amounts because the entire track moves. However, in some embodiments, by using a track system with independently operating sections that can respond to individual carriers, or individual carriers that have independent motive capability, the acceleration of any given carrier can be tailored to limit acceleration/deceleration and jerk, while allowing the average velocity to be greater than that of traditional tracks. By not limiting the top speed of a carrier, the carrier can continue to accelerate on each track section, as appropriate, resulting in a substantially higher average speed around the track. This can assist the carrier in traversing the entire track system in less than one machine cycle of the analyzer. These machine cycles can be, for instance, 20 or 40 seconds.

Similarly, an autonomous carrier can know its own identity and that of its payload. This allows the carrier to actively participate or assist in the routing decision process at individual decision points. For example, upon reaching a decision point (e.g., switch, intersection, junction, fork, etc.), a carrier can communicate its identity and/or the identity of its payload to the track or any switching mechanism (or its intended route that the carrier has determined based on the payload identity), via RF or near-field communication. In this scenario, the carrier does not need to be stopped at a decision point for a barcode scan. Instead, the carrier can keep going, possibly without even slowing down, and the carrier can be routed in real time. Furthermore, if the carrier knows where it is going or communicates its identity to the track (such that the track knows where the carrier is going) before the carrier physically reaches a decision point, the carrier can be made to decelerate prior to a decision point if the carrier will be turning. On the other hand, if the carrier does not need to turn at the decision point, the carrier can continue at a higher velocity because the sample carried by the carrier will not undergo cornering forces if the carrier is not turning at the decision point or a curved section of the track.

An autonomous carrier can also include onboard processing and sensor capabilities. This can allow the carrier to determine where it is on the track and where it needs to go, rather than being directed by the track (although, in some embodiments a central controller sends routing instructions to the carrier to be carried out). For example, position encoding or markers in the track can be read by the carrier to determine a carrier's location. Absolute position information can be encoded on a track surface to provide reference points to a carrier as it traverses the track. This position encoding can take many forms. The track may be encoded with optical markers that indicate the current section of the track (e.g., like virtual highway signs), or may further include optical encoding of the specific absolute location within that section of track (e.g., like virtual mile markers). Position information can also be encoded with markings between absolute position marks. These can provide synchronization information to assist a carrier in reckoning its current trajectory. The optical encoding scheme may take on any appropriate form known to one skilled in the art. These marks used by the encoding scheme may include binary position encoding, like that found in a rotary encoder, optical landmarks, such as LEDs placed in the track at certain positions, barcodes, QR codes, data matrices, reflective landmarks, or the like. General position information can also be conveyed to the carrier via RF/wireless means. For example, RFID markers in the track can provide near field communication to the carrier to alert the carrier that it has entered a given part of the track. In some embodiments, local transmitters around or near the track can provide GPS-like positioning information to enable the carrier to determine its location. Alternatively, sensors in the track, such as Hall effect sensors or cameras, can determine the position of individual carriers and relay this information to the carrier.

Similarly, the carrier can have sensors that indicate relative motion, which provide data that can be accumulated to determine a position between absolute position marks. For example, the carrier may have gyroscopes, accelerometers, or optical sensors that observe speckle patterns as the carrier moves to determine velocity or acceleration, which can be used to extrapolate a relative position. In some embodiments, components include a light source and image sensor, and can be used to observe the relative motion of the track surface with respect to the carrier to determine a real-time trajectory estimate. For example, after reckoning its position with an absolute position mark, the carrier can observe successive images of a track surface and compare these images to determine the direction and magnitude of motion. This can be used to determine real-time position, velocity, acceleration, and jerk, or estimates thereof. In addition, synchronous marks, such as marks placed at regular intervals in the track, can be used to reckon the carrier's position between absolute position marks and can correct errors that may have accumulated in the real-time trajectory information determined from observation of the relative motion of the surface of the track. This can allow a lower sampling frequency or less precise components in the position decoding imaging sensor.

Because a carrier can know where it is and its motion relative to the track, a carrier can essentially drive itself, provided it knows its destination. The routing of the carrier can be provided in many different ways in various embodiments. In some embodiments, when a carrier is loaded with the sample, the system can tell the carrier the destination analyzer station. This information can be as simple as the identification of the destination station in embodiments where the carrier has autonomous routing capability. This information can also be detailed information such as a routing list that identifies the specific path of the individual track sections and decision points that a carrier will traverse. Routing information can be conveyed to the carrier via any communication method described herein, such as RF communication, near-field/inductive communication, electrical contact communication, or optical communication.

In an exemplary embodiment, when an operator scans the barcode of the sample tube and places it in a carrier, the system determines the identity of the carrier and matches it with the identity of the sample. The system then locates the record for the sample to determine which tests the sample must undergo in the analyzer. A scheduler then allocates testing resources to the sample, including choosing which tests will be done by individual testing stations and when the sample should arrive at each testing station for analysis. The system can then communicate this schedule (or part of the schedule) to the carrier to inform the carrier of where it needs to go, and optionally, when it needs to go and/or when it needs to arrive.

Once the carrier is placed onto the track system, the routing capabilities and location acquisition systems of the carrier enable the carrier to determine where it is on the track and where it needs to go on the track. As the carrier traverses the track, the carrier reaches individual decision points and can be directed along the main track or along sub-paths as appropriate. Because each carrier operates independently from one another, a carrier can do this quite quickly without necessarily stopping at each decision point and without waiting for other carriers in a queue. Because these carriers move quickly, there is less traffic on the main sections of the track, which reduces the risk of collision or traffic jams at decision points or corners in the track (e.g., sections where carriers might slow down to avoid excessive forces on the sample).

Motive force can be provided to the carriers in many ways. In some embodiments, the track actively participates in providing individualized motive force to each carrier. In some embodiments, motive force is provided by electromagnetic coils in the track that propel one or more magnets in the carrier. An exemplary system for providing this motive force is the track system provided by MagneMotion, Inc., which can generally be understood by the description of the linear synchronous motors (LSMs) found in US Published Patent Application 2010/0236445, assigned to MagneMotion, Inc. These traditional systems utilizing this magnetic motion system have included passive carriers that lack the integrated intelligence of the carriers described herein, and all routing and decisions are made by a central controller with no need for active carriers that participate in the routing and identification process.

In embodiments that utilize magnetic motion, the electromagnetic coils and the magnets operate as an LSM to propel each individual carrier in the direction chosen with precise control of velocity, acceleration, and jerk. Where each coil on the track (or a local set of coils) can be operated independently, this allows highly localized motive force to individual carriers such that individual carriers can move with their own individually tailored accelerations and velocities. Coils local to a carrier at any given moment can be activated to provide precise control of the direction, velocity, acceleration, and jerk of an individual carrier that passes in the vicinity of the coils.

In some embodiments, a track may be comprised of many individually articulable rollers that act as a locally customizable friction track. Because individual micro-sections of the track can be managed independently, rollers immediately around a carrier may be controlled to provide individualized velocity, acceleration, and jerk. In some embodiments, other active track configurations can be used that provide localized individual motive force to each carrier.

In some embodiments, the track may be largely passive, providing a floor, walls, rails, or any other appropriate limitations on the motion of a carrier to guide the carrier along a single dimension. In these embodiments, the motive force is provided by the carrier itself. In some embodiments, each individual carrier has one or more onboard motors that drive wheels to provide self-propelled friction-based motive force between the track and the carrier. Unlike traditional friction tracks, where the track is a conveyor, carriers with driven wheels can traverse the track independently and accelerate/decelerate individually. This allows each carrier to control its velocity, acceleration, and jerk at any given moment to control the forces exerted on its payload, as well as traverse the track along individually tailored routes. In some embodiments, permanent magnets may be provided in the track and electromagnets in the carrier may be operated to propel the carrier forward, thereby acting as an LSM with the carrier providing the driving magnetic force. Other passive track configurations are also contemplated, such as a fluid track that allows carriers to float and move autonomously via water jets or the like, a low friction track that allows carriers to float on pockets of air provided by the track, (e.g., acting like a localized air hockey table), or any other configuration that allows individual carriers to experience individualized motive forces as they traverse the track.

Figure 5:
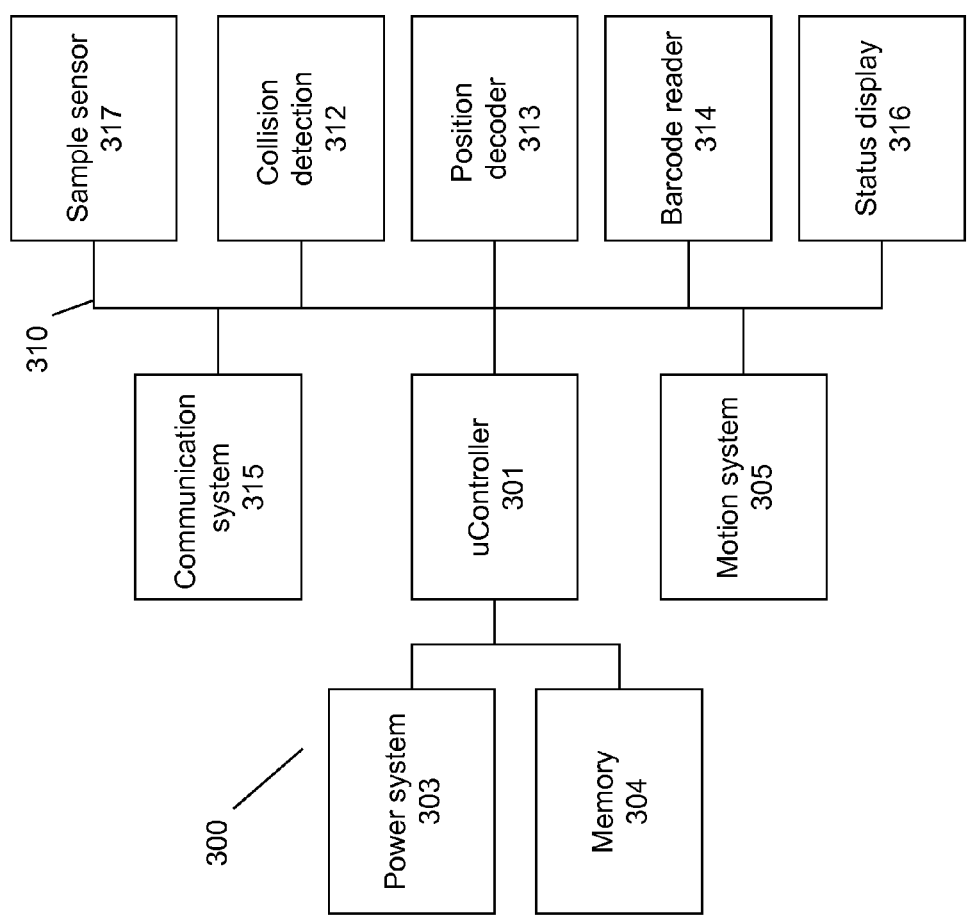
FIG. 5 is a system block diagram of control systems including onboard active carriers that can be used with certain embodiments disclosed herein.

FIG. 5 shows a top-level system diagram of the control systems and sensors for an exemplary intelligent autonomous carrier 300. Carrier 300 is controlled by a microcontroller 301 that includes sufficient processing power to handle navigation, maintenance, motion, and sensor activities needed to operate the carrier. Because the carrier is active and includes onboard electronics, unlike prior art passive carriers, the carrier includes an onboard power station. The details of this station vary in different embodiments of the present invention. In some embodiments, power system 303 comprises a battery that may be charged as the carrier operates, while in other embodiments, the battery is replaceable or can be manually charged when the carrier is not operating. Power system 303 can include the necessary charging electronics to maintain a battery. In other embodiments, the power system 303 comprises a capacitor that may be charged by inductive or electrical contact mechanisms to obtain electrical potential from the track itself, in much the same way a subway car or model train might receive power.

Microcontroller 301 communicates with system memory 304. System memory 304 may include data and instruction memory. Instruction memory in memory 304 includes sufficient programs, applications, or instructions to operate the carrier. This may include navigation procedures as well as sensor handling applications. Data memory in memory 304 can include data about the current position, speed, acceleration, payload contents, navigational plan, identity of the carrier or payload, or other status information. By including onboard memory in carrier 300, the carrier can keep track of its current status and use information to intelligently route around the track or convey status information to the track or other carriers.

Microcontroller 301 is responsible for operating the motion system 305, sensors 312, 313, and 314, and communication system 315, status display 316, and sample sensor 317. These peripherals can be operated by the microcontroller 301 via a bus 310. Bus 310 can be any standard bus, such as a CAN bus, that is capable of communicating with the plurality of peripherals, or can include individual signal paths to individual peripherals. Peripherals can utilize their own power sources or the common power system 303.

Motion system 305 can include the control logic necessary for operating any of the motion systems described herein. For example, motion system 305 can include motor controllers in embodiments that use driven wheels. In other embodiments, motion system 305 can include the necessary logic to communicate with any active track systems necessary to provide a motive force to the carrier 300. In these embodiments, motion system 305 may be a software component executed by microcontroller 301 and utilizing communication system 315 to communicate with the track. Devices such as motors, actuators, electromagnets, and the like, that are controlled by motion system 305 can be powered by power system 303 in embodiments where these devices are onboard the carrier. External power sources can also provide power in some embodiments, such as embodiments where an LSM provides motive force by energizing coils in the track. In some embodiments, motion system 305 controls devices on or off the carrier to provide motive force. In some embodiments, the motion system 305 works with other controllers, such as controllers in the track, to coordinate motive forces, such as by requesting nearby coils in the track be energized or requesting the movement of local rollers. In these embodiments, motion system 305 can work together with communication system 315 to move the carrier.

Carrier 300 can include one or more sensors. In some embodiments, carrier 300 includes a collision detection system 312. Collision detection system 312 can include sensors at the front or back of a carrier for determining if it is getting close to another carrier. Exemplary collision detection sensors can include IR range-finding, magnetic sensors, microwave sensors, or optical detectors. Whereas many prior art pucks are round, carrier 300 may be directional, having a front portion and a rear portion. By having a directional geometry, carrier 300 can include a front collision detector and a rear collision detector.

In some embodiments, collision detection information can include information received via the communication system 315. For example, in some embodiments, the central controller for the track can observe the location and speed of carriers on the track and evaluate collision conditions and send updated directions to a carrier to prevent a collision. In some embodiments, nearby carriers can communicate their positions in a peer-to-peer manner. This allows carriers to individually assess the risk of collision based on real-time position information received from other carriers. It will be understood that in embodiments where the carrier receives trajectory information about other carriers, or decisions are made with the help of a centralized controller that has access to trajectory information of nearby carriers, the carriers need not be directional, and can include sensors or receivers that do not depend on a given orientation of a carrier.

Carrier 300 can also include a position decoder 313. This sensor can extrapolate the carrier's position as described herein. For example, position decoder 313 can include a camera or other optical means to identify landmarks in the track, observe optical encoding in the track, and observe the instantaneous relative motion of the track. In some embodiments, position decoder 313 can also include inertial sensors, magnetic sensors, or other sensors sufficient to determine a carrier's current position, direction, velocity, acceleration, and/or jerk. In some embodiments, the components of the position decoder 313 can operate as part of the communication system. For example, in some embodiments, optical markings in the track can be electronically rewriteable, such as via an LCD or E-Ink display, and can be used by a central controller to convey routing instructions, along with position information. In these embodiments, image sensors used to determine position can also be used to receive the routing instructions or other data being communicated to the carrier.

Carrier 300 can optionally include a barcode reader 314. If equipped with the barcode reader 314, carrier 300 can observe the barcode of its payload at the time the samples are loaded onto the carrier or at any time thereafter. This prevents the need for a carrier to stop at individual decision points to have the system read the barcode of a sample tube. By reading and storing the identity of the sample tube, or conveying this information to the overall system, a carrier may more efficiently traverse the track system because routing decisions can be made in advance of reaching a decision point. Alternatively, where a system knows the identity of the sample when it is placed onto the carrier, the system can include an external barcode reader and can convey the identity of the payload to the carrier for storage and memory 304 via communication system 315.

Communication system 315 can comprise any mechanisms sufficient to allow the carrier to communicate with the overall automation system. For example, this can include an XBee communication system for wireless communication using an off-the-shelf communication protocol, such as 802.15.4, any appropriate version of 802.11, or any standard or proprietary wireless protocol. Communication system 315 can include a transceiver and antenna and logic for operating an RF communication protocol. In some embodiments, communication system 315 can also include near-field communication, optical communication, or electrical contact components. Information conveyed via the communications system to/from carrier 300 is described throughout this application.

In some embodiments, the carrier can also include a status display module 316. The status display module 316 can include a controller and rewritable electronic display, such as an LCD panel or E-ink display. In some embodiments, the controller is treated as an addressable portion of memory, such that the microcontroller 301 can easily update the status display 316.

In some embodiments, the carrier also includes sample sensor 317. This sensor can be used to indicate the presence or absence of a fluid container in the carrier's tube bracket (which may also be referred to as a tube holder). In some embodiments, this is a momentary mechanical switch that is depressed by the presence of a tube and not depressed when a tube is absent. This information can be used to determine the status of a tube, which can assist in the display of status information by status display module 316.

Routing

The desire for rapid transit times within an analyzer system can make routing difficult. In prior art systems, rapid routing is less critical because samples are generally stopped, singulated, and scanned at each decision point. In those systems, the routing decision for a given decision point can be made while the sample is stopped. Rapid routing decisions are generally desired, and may require determining a switching decision before a sample carrier reaches a decision point. Furthermore, because the carriers move at a rapid rate compared to the prior art, the control of the instantaneous trajectory of a sample carrier can be assisted by real-time processing in order to prevent spilling or damaging IVD samples. In some embodiments, substantially instantaneous trajectory observation and control is conducted onboard each carrier to facilitate real-time control, while the overall routing decisions are made by a central controller that manages a group of carriers. Therefore, in some embodiments of the present invention, the carriers act like semi-autonomous robots that receive global routing instructions from a central controller, but make local motion decisions substantially autonomously.

For example, when a carrier receives a sample (e.g., a patient fluid sample or other payload) a central controller managing one or more carriers determines the schedule for that carrier and instructs the carrier where to go on the track of, for example, an in vitro diagnostics automation system. This instruction can be a next-hop instruction (e.g., identifying the next leg of a route), such as going to a given decision point, moving forward to the next decision point, or turning at a given decision point. In some embodiments, the instructions can include a complete or partial list of track segments and decision points to be traversed and whether to turn at each decision point. These instructions can be communicated to the carrier from a central controller via any conventional means, including wireless or contact electrical signaling, as explained throughout this disclosure.

Because the carriers are actively involved in routing and trajectory control, the carriers should have a way to determine position and velocity information as they traverse the track, for example, of an IVD automation system. While accelerometers can provide acceleration information that can be integrated to determine a relative velocity and position, the precision of this information may be insufficient to be reliable for positioning carriers, and the samples they carry, at certain points in the system. For example, a pipette may need to be accurately placed in a tube on the carrier without contacting the walls of the tube. Therefore, it may be desirable to accurately position a carrier and its payload within about a millimeter at certain points on the track. In other sections of the track, such as straightaways, precise absolute position encoding may not be necessary.

In some embodiments, optical encoding on the track (e.g., on or in one or more track surfaces) can be used to provide position and/or velocity information to the carrier. Because the need for precision in the positioning information can vary throughout the system, some embodiments forego unnecessary encoding precision in portions of the automation system. In some embodiments, the natural surface characteristics in the track itself can be used for positioning encoding. This may allow an imaging device on the carrier to track the relative motion of the track surface as the carrier moves in areas where precise absolute positioning is unnecessary, such as straightaways or track sections between decision points. This natural encoding can be supplemented by placing synchronization marks at known intervals throughout the track. For example, in an area where coarse trajectory information is acceptable, natural pitting and other texture of the surface can be used for navigating between two absolute position marks (such as marks placed at a pipette or a decision point). Meanwhile, marks distinguishable from the surface texture can be placed at regular intervals, such as every 10 cm, to provide synchronization information and correct any error that may accumulate from observing the relative motion of the track surface.

Using position and/or velocity information obtained through observing the track (and any encoding), each carrier can follow routing instructions to reach destinations in the track system quickly, accurately, and without damaging or spilling samples being carried thereon. This position information can be used with information about the topography of the track and physical properties of the carrier's payload to determine the appropriate acceleration and velocity at any moment to minimize lateral forces on curves or allow the carrier to brake with sufficient distance to stop at intended destinations. In addition to position information, the carrier can make trajectory decisions, while following the instructions, each carrier can make a determination of the appropriate velocity, acceleration, and jerk (as used herein, acceleration includes deceleration). This can include a real-time decision of whether the carrier must slow down to avoid collision or to enter a curve without causing excessive lateral forces, or slow down before the next decision point. These decisions can be made with the assistance of any onboard sensors, as well as external information received by the carrier, such as information about the position and trajectory of nearby carriers. For example, accelerometers and track encoding information can be used to determine the current velocity, acceleration, and jerk, as well as the current position of a carrier. This information can be used by each carrier to determine its trajectory and/or can be conveyed to other carriers.

Figure 6:
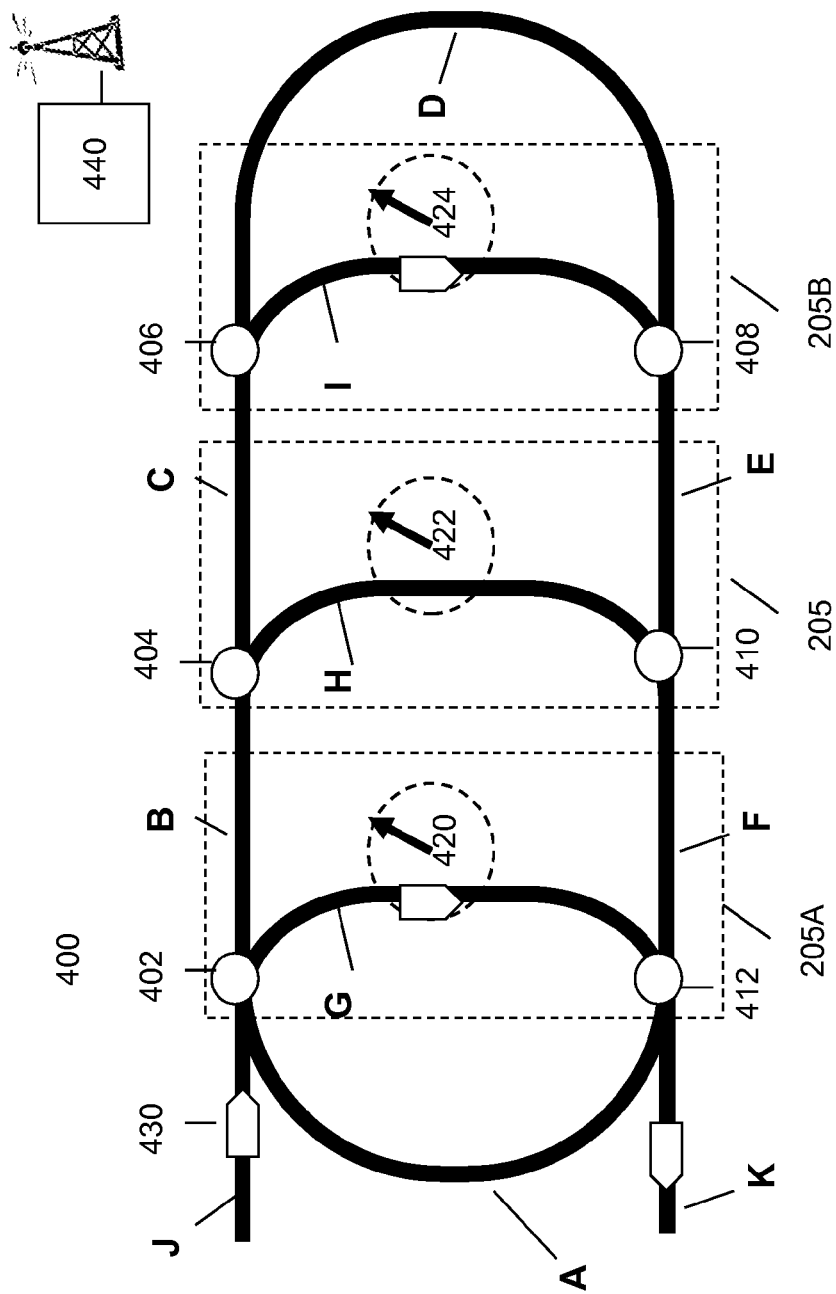
FIG. 6 is a diagrammatic view of exemplary routes in an exemplary track configuration that can be used for navigation of sample carriers in certain embodiments.

FIG. 6 shows an exemplary routing scenario in automation track system 400. Carrier 430 receives routing instructions from central management controller 440 via RF signaling. Carrier 430 can be any suitable embodiment of a carrier, such as carrier 300, shown in FIG. 5. Central management processor 440 can be a microprocessor, software operating on one or more processors, or other conventional computer means suitable for calculating the schedule for multiple carriers within the track system 400. Central management processor 440 can receive position information from multiple carriers, as well as any sensor information from sensors in the track system 400 and/or information reported by the carriers. Central management processor 440 uses the status information of the carriers and track as well as the identity of samples or other payload carried by the carriers and the required assays to be performed by the system on these samples.

The exemplary track 400 shown in FIG. 6 includes a first curve segment A that connects to straight segment B and a pullout segment G (e.g., a segment that serves a testing station), which serves analyzer/testing station 205A and pipette 420, via decision point 402. Segment B connects to straight segment C and a pullout segment H, which serves analyzer/testing station 205 and pipette 422, via decision point 404. Segment C connects to curved segment D, which serves sample handling stations 205C, and pullout segment I, which serves analyzer/testing station 205B and pipette 424, via decision point 406. Segment D connects to straight segment E and the other end of pullout segment I, via decision point 408. That is, there are different paths between decision points 406 and 408—segments D and I, (where segment I is a pullout that can be used to deliver samples to interact with pipette 424). Segment E connects to straight segment F and the other end of pullout segment H, via decision point 410. Segment F connects to curved segment A and the other end of pullout segment G, via decision point 412. In some embodiments, track 400 includes input and output lanes J and K, which can be used to add or remove carriers at decision points 402 and 412.

In some embodiments, decision points 402-412 are passive forks in the track that carrier 430 can navigate to select a proper destination segment. In other embodiments, decision points 402-412 are active forks that can be controlled by carrier 430 or central management processor 440. In some embodiments, decision points 402-412 are electromagnetically controlled switches that respond to requests by carrier 430, such as via RF or near-field communication. In some embodiments these electromagnetically controlled switches have a default position, such as straight, that the switch will return to once a carrier has been routed. By using default positions for decision points, a carrier may not need to request a position at each decision point, unless it needs to be switched at that decision point.

Scheduler central management processor 440 assigns carrier 430 to a first route, Route 1, to place the carrier 430 and its payload within reach of pipette 420. Carrier 430 is instructed to travel along segment J to decision point 402 and travel onto segment G to stop at a position accessible to pipette 420. In some embodiments, carrier 430 receives the instructions and determines its current location and trajectory to determine a direction and trajectory to use to reach decision point 402. Carrier 430 can also take into account that it will be making a hard right turn at decision point 402 onto segment G. In some embodiments, decision point 402 includes a switching mechanism in the track that can operate under the control of carrier 430. In these embodiments, carrier 430 communicates with the track on approach to decision point 402 to request switching onto segment G. In other embodiments, carrier 430 may have a steering mechanism (such as moveable guide wheel, directional magnets, asymmetric brakes, or the like) that allows carrier 430 to make a right turn onto segment G at decision point 402, without the assistance of an external gate integrated into the track. In these embodiments, carrier 430 engages the steering mechanism at decision point 402 to make the turn onto segment G.

This determination can be based on observing the position encoding in the track, including consulting the onboard memory of the last known position. Near-field communication from the track can also be used to provide an identification of the current track and encoding scheme being used by the track. Carrier 430 can take into account that it will be making a hard right turn at decision point 402 onto segment G. Using position encoding, carrier 430 can determine where it is in relation to decision point 402 on track J and adjust this trajectory accordingly, to ensure that it approaches the decision point with appropriate velocity.

Carrier 430 can determine its rough location—its current track section, such as section J, by reading encoding in the track, such as optical encoding, or RFID tags. In some embodiments, carrier 430 uses multiple means to determine its location within the track system 400. For example, RFID tags can be used to determine generally on which track segment the carrier 430 is located, while optical encoding or other precise encoding can be used to determine the position within that track segment. This encoding can also be used to determine velocity, acceleration, or jerk by observing changes in the encoding (e.g., derivatives from the position information).

Carrier 430 can use the identification of the current track section to determine the appropriate route to the destination section either by explicit instruction received by the central management processor 440 or by looking up an appropriate route in an onboard database in memory 304, as shown in the onboard control systems in FIG. 5. In some embodiments, the carrier 430 has an understanding of how to reach section G from section J based on a map stored in the memory of carrier 430 in memory 304. This map can include a simple lookup table or a tree of track sections where each node is linked by the corresponding decision points, or vice versa. For example, upon identifying that the carrier is currently in the track section J, the onboard database can inform carrier 430 to proceed to decision point 402 to be switched to the right onto section G.

Optical Navigation

In the exemplary embodiment shown in FIG. 6, near-field communication (e.g., RFID) can be used to convey the current track section, such as sections A-K, to a carrier 430 when it enters that section by placing RFID tags at the entrance to a track section. The identification of the track section can also be conveyed via optical marks. These optical marks can act like signposts, identifying the track section the carrier is entering. These marks can also convey an absolute position (e.g., the precise starting point of the track section or any known position within the track system, such as a decision point or pipette location).

These marks can be applied cost effectively (e.g., relatively inexpensively) to the track by any conventional means including, for example, using stickers, painting, etching, etc. the marks onto the track surface to provide a static mark. These marks may also be active elements including, for example, LCDs, LEDs, etc. placed in the surface of the track to provide reference points, and allow some ability to change the markings dynamically. For example, in a given configuration, a certain location of the track section may be an important absolute position. However, in other configurations, or for certain carriers, the position may not have importance. In those instances, an active mark can be rewritten and/or turned off.

In some embodiments, marks are provided by a rewriteable surface, such as a series of E-ink, LCD, or OLED panel displays. This may allow a central controller to update the marks dynamically or, as part of a configuration scheme, to convey dynamic content to the carriers, such as individualized routing instructions, or as part of a system configuration scheme. For example, a position within an analyzer may have significance when the analyzer is in a certain mode or configuration, such as a test mode.

In some embodiments, marks may not be black and white or other well defined two-toned combinations. For example, in some embodiments, the size of the mark varies along the track. The size of the mark can be used to convey information, such as using certain distinct marks for absolute position information, while using smaller marks repeatedly (e.g., every 10 cm or other suitable distance), to synchronize positions between absolute position marks. By using synchronization marks, the encoding scheme can ensure that carriers do not accumulate errors when observing the relative motion of the track surface between absolute position marks. Absolute position marks can be of any suitable size relative to the size of the carrier and carrier optics. In some embodiments, each mark is sized by the carrier to be visible within a single frame. In some embodiments, each mark is less than 1 cm.

In other embodiments, marks can be of multiple colors. The color of marks can convey certain information, such as the synchronization pitch of the encoding or the current track section. For example, black and white marks may be used in areas where high precision is needed, such as around pipettes, while red and white marks may be used on track sections that are near decision points or curves to indicate to a carrier that it should slow down. That is, the color can act as a warning. Similarly, encoding after obstacles such as decision points may be colored green to convey to carriers that it is an appropriate area to accelerate. In other embodiments, black and white marks may be of a certain known pitch, while red and white marks are of a rougher pitch. Marks can be also reflective or made to absorb light on an otherwise reflective surface.

In addition to black and white marks (or any other contrasting color combination), a track 400 can convey position information via other artifacts. For example, the track can include landmarks, such as LEDs, or optical symbols that stand out from the track surface. Landmarks can indicate important features in the track, such as a stopping point for a test station, a braking zone entering a curve, or a braking zone approaching a decision point. Landmarks can be a type of absolute position mark.

As the carrier begins iteratively implementing its planned trajectory, it observes the track for upcoming landmarks, such as its terminal destination or an upcoming decision point at step 520. These landmarks can be identified via important upcoming decisions point at step 520. These landmarks can be identified via important features in the track, such as a stopping point for a test station, a braking zone entering a curve, or a braking zone approaching a decision point. Landmarks can be a type of absolute position mark warning or braking LED, by extrapolating the distance to a landmark from the observed encoding, or by some combination thereof. If no landmark is upcoming, the carrier continues to step 504 and continues to iteratively calculating and implementing a planned trajectory.

In this example, there are two types of important landmarks. The first landmark may include the destination of the carrier. The carrier can determine if it is nearing its destination based on track encoding or a landmark feature, such as an LED, and uses this information to begin stopping or complete a stopping procedure. For example, a carrier may be instructed to stop at a precise location accessible to a pipette. This precise location may include an LED in the wall or floor of the track to assist a carrier in the stopping at a precise location with millimeter accuracy. In some embodiments, a carrier observes the track surface (e.g., surface texture and synchronization marks) to calculate rough trajectories, sufficient to move the carrier in a rough location of its destination. An absolute position mark can provide precise encoding to locate an exact destination.

Another available landmark could indicate a decision point. Using warning LEDs or marks as encoding in the track can convey the position of an upcoming decision point to a carrier relative to the carrier's current location. LEDs can provide dynamic encoded information. For example, a central scheduler may illuminate an LED at a braking position on the track some distance before a decision point. This can alert the carrier to decelerate to prevent unnecessary acceleration or collision. In some embodiments, if the carrier is not scheduled to turn at a decision point, the central scheduler can refrain from illuminating an LED. A carrier that does not need the landmark can simply ignore the landmark. Braking landmarks can serve as a failsafe to rectify a carrier's trajectory before turning. If the carrier will be turning and it observes a landmark that it did not expect, it can indicate that the extrapolated location perceived by the carrier is false. It may be necessary to update the trajectory to begin decelerating so that the velocity of the carrier is slow enough when it turns at the decision point to prevent unnecessary lateral forces that could harm or spill a sample.

Figure 7C:
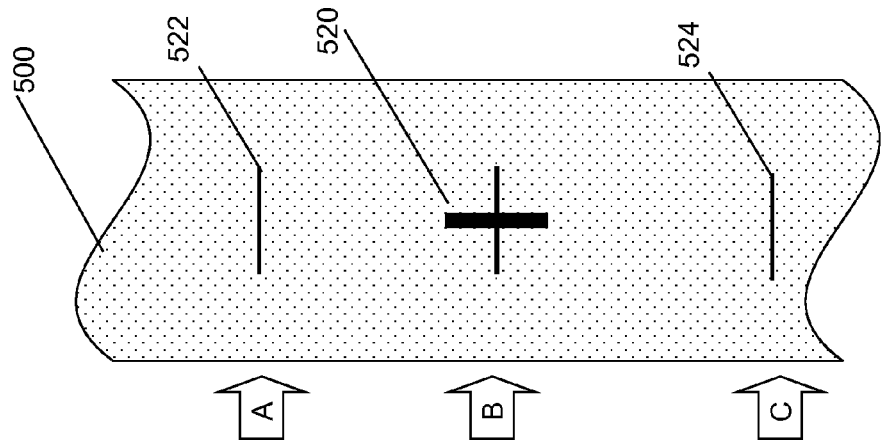
FIG. 7C is a head-on view of an exemplary track surface having position marks for use with certain embodiments.
Figure 7B:
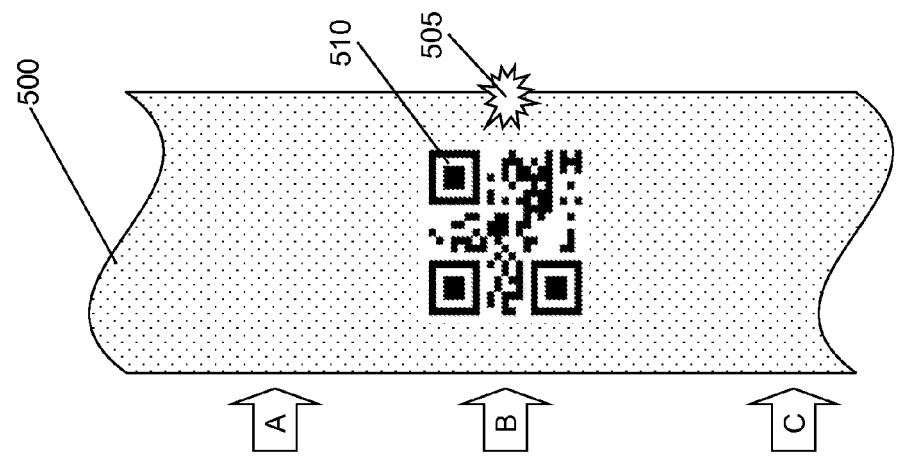
FIG. 7B is a head-on view of an exemplary track surface having a position mark for use with certain embodiments.
Figure 7A:
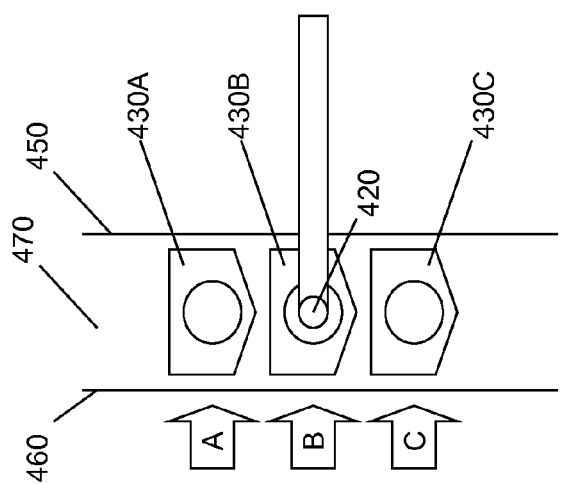
FIG. 7A is a top view of an exemplary track section for use with embodiments of an encoding scheme.

FIG. 7A illustrates different positions at which a carrier 430 can stop. In this example, pipette 420 operates a small sample queue. Motion of the carriers in the queue can be constrained by surfaces 450, 460, and 470. Here, carrier 430A stops before pipette 420 at position A. Meanwhile, carrier 430B stops at position B directly under pipette 420. This allows pipette 420 to interact with the sample carried by carrier 430B. Carrier 430B may be required to stop within a precise location with respect to position B to allow pipette 420 to accurately interact with the sample. For example, a precise location may include locating carrier 430B within a millimeter of position B. In other embodiments, more precise positioning may be provided, for example, in one embodiment within 0.5 mm; and, for example, in another embodiment within 0.1 mm. If the local queue is random access, another carrier 430C may be positioned at position C while it waits to interact with pipette 420 at position A or B. The exemplary station shown in FIG. 7A may include testing station 205A (see FIG. 6), but similar examples may exist at the stations served by pipettes 422 and 424.

To achieve precise position encoding around pipette 420, the marks shown in FIG. 7B or 7C may be used. In the example shown in FIG. 7B, two types of absolute position marks are used. QR code 510 is placed on track surface 500 to provide a precise location for position B. It should be noted that QR codes inherently have precise positioning information within the structure of the mark. For example, the large square features of QR code 510 provide reference positions within the mark itself, as well as providing orientation information. Similarly, in some embodiments, a light source, such as LED 505, can also be provided at position B to add further or alternative precision. In other embodiments, no LED is used as the QR code 510 provides sufficient absolute positioning information. Marks 510 and 505 need not be on the same track surface (but can be in some embodiments). For example, one could be on the floor of the track, while one may be on the wall track. In this example, positions A and C are any known distance from position B, and a carrier 430 can utilize the natural surface texture of track surface 500 to observe the relative motion of the carrier over the track surface to move a short distance between position B and position A with relative precision, as explained below.

FIG. 7C shows an alternate example of positioning marks sufficient to indicate positions A, B, and C. As shown in FIG. 7C, an absolute positioning mark 520 can be placed on surface 500. In this example, absolute position mark 520 is a two-dimensional radical style mark. This can be used to provide longitudinal and lateral position information to carrier 430. For example, in an embodiment where a carrier has freedom of movement along the track as well as transversely to the track, this two-dimensional information can be quite useful. It should be noted that in embodiments that have lateral freedom of movement, this embodiment may not necessarily have large degrees of freedom of movement laterally. For example, embodiments where a carrier has its own steering mechanism and is not necessarily physically guided by track walls, a carrier's lateral position may vary by a few millimeters or centimeters along the length of track. Lateral positioning information can then be used to correct its trajectory or to convey the deviation in the lateral placement of a sample to a sample pipette so that a lateral adjustment can be made by the pipette when interacting with the sample.

Between absolute position marks, track surface 500 can include relative position markers, such as synchronization marks. Marks 522 and 524 shown in FIG. 7C are examples of synchronization marks. In one exemplary embodiment, synchronization marks may be placed along a track at predetermined intervals, e.g., every 10 cm. In such an embodiment, positions A and C would correspond to synchronization marks 522 and 524, respectively, of FIG. 7C, where position A is 10 cm away from position B, for example. In contrast to the exemplary embodiment shown in FIG. 7B, synchronization marks 522 and 524 can also act as absolute position marks at position A and position C, respectively, such that a carrier need not rely on precision in its observation of relative movement of the track to correctly position itself at position A or position C. It should be appreciated that the exemplary embodiment in FIG. 7B may also include synchronization marks, which may or may not be at positions A and C.

Figure 8B:
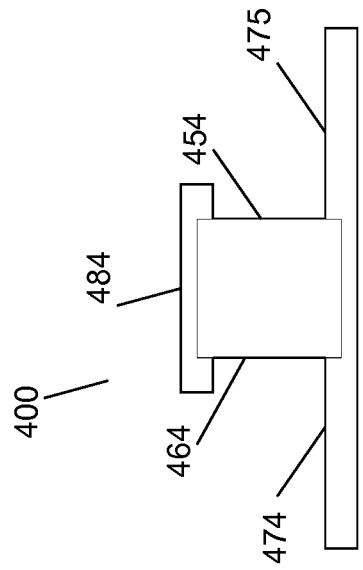
FIGS. 8A and 8B are cross-sectional views of exemplary tracks used with embodiments of an encoding scheme.
Figure 8A:
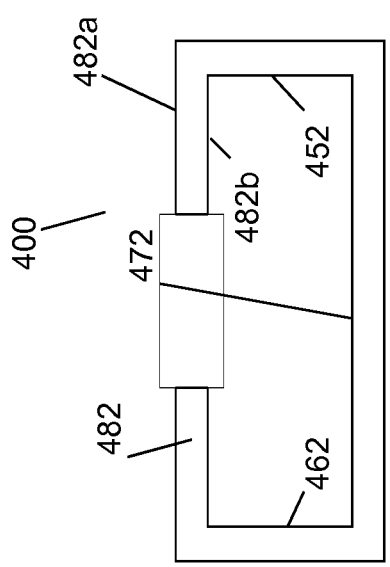

FIGS. 8A and 8B show cross-sections of exemplary tracks 400 that can be used with the present invention. These cross-sections have multiple surfaces that can be used for encoding position information. For example, FIG. 8A shows a trough-like track having a bottom surface 472, a right surface 452, a left surface 462, and at least one top surface 482, top surface 482 also having an upper surface 482A and lower surface 482B. Any of these surfaces may be chosen for encoding position marks. A suitable carrier that travels on this track can then include photodetectors or other optical detectors positioned to observe the marks. The track in FIG. 8B is a monorail-type structure. This track has respective right and left bottom surfaces 475 and 474, respective right and left vertical faces 454 and 464, and at least one top surface 484. Similarly, any of these surfaces can be chosen as appropriate for encoding position information.

Position marks can be applied to any of these surfaces in any suitable manner. In some embodiments, this can include applying a sticker or label, etching, painting, marking, changing a reflective property, applying an electronically rewritable surface to the track, or by any other suitable means.

Figure 9:
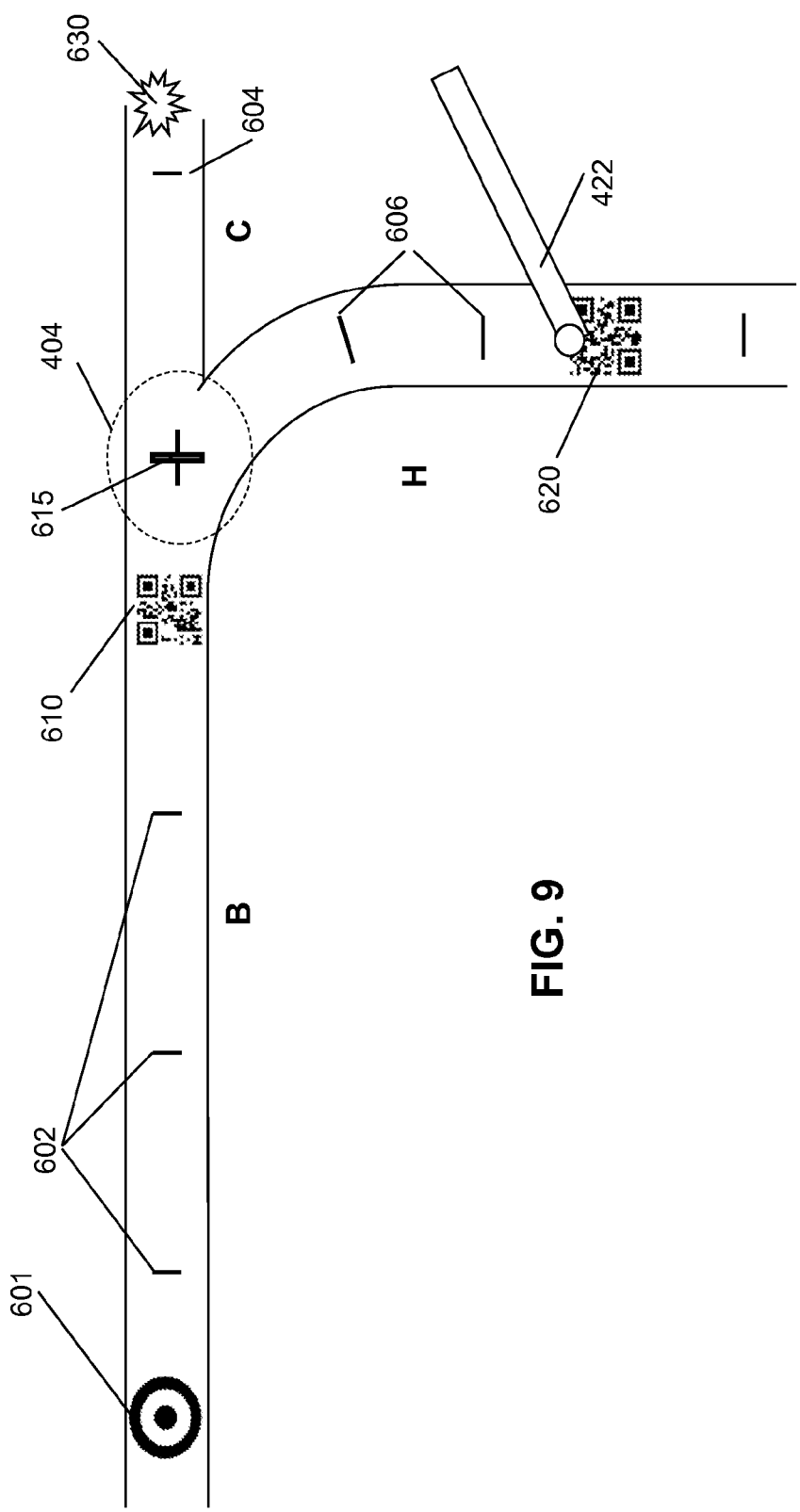
FIG. 9 is a top view of an exemplary track section employing position marks for use with certain embodiments.

FIG. 9 shows an example of mark placement within a track system, such as that shown in FIG. 6. Upon entering a section B, a carrier may observe a reference mark 601, which may be a two-dimensional bulls-eye pattern. This can be used for two-dimensional reckoning of a carrier as it enters a track section. Mark 601 may act as an absolute position mark. After observing mark 601, a carrier can proceed by observing the relative motion of the track as it traverses the track. This can include observing the motion of shadows created from an off-axis light source using an imaging device and comparing successive frames to note the motion of features within the image. This can provide relative accuracy in estimating a current trajectory and for extrapolating a current position within track section B.

Synchronization marks 602 may be provided at regular intervals on the track surface of section B. By placing synchronization marks 602 at regular intervals, any drift in positional accuracy due to imprecision in the observation of the relative motion of the track as the carrier traverses can be corrected or accounted for. This error can be an accumulation of sampling error, such as due to frame rate and image inaccuracies (such as blurry images or a low-resolution) or due to image processing errors (such as erroneous correlation of image artifacts). By providing robustness against errors in observing relative motion of the carrier to the track surface (and/or correcting such errors), lower precision imaging sensors may be employed, which may reduce the cost of implementing the carriers. Furthermore, while estimates of velocity from observing texture features in the track surface may be suitable for routing the carrier without spilling a sample and a real-time estimation of position and trajectory, synchronization marks can provide additional positional accuracy at low cost.

In the example shown in FIG. 9, prior to reaching a decision point 404, position mark 610 can provide information to a carrier about the upcoming decision point 404. Mark 610 may be an absolute position mark in the form of a QR code, for example. A QR code can include many bits of data within the binary patterning present in an image. The amount of information that can be conveyed by the QR code depends on the resolution of the binary information in the QR code. For example, a version 1 QR code provides a 21×21 pixel image, while a version 4 QR code includes a 33×33 pixel image, which can convey up to 50 characters of information with error correction. Any suitably sized QR version can be chosen and any known QR encoding scheme can be used, as suitable for the application. For example, a lower resolution QR code may be used to reduce the cost of the imaging sensors used in carriers if large amounts of information do not need to be conveyed in a single QR code. As more accurate imaging sensors become available (e.g., cheaper), denser QR codes may be easily used with some embodiments. QR codes can be advantageous for use with embodiments of the present invention because of the built-in error coding to provide robustness, while also including readily distinguishable features that provide positional and orientation reference points to a carrier (e.g., the fixed bulls-eye patterns in the corners of the QR code).

In this example, QR code 610 may be used for both position and to convey information about decision point 404 to the carrier with enough time for the carrier to navigate appropriately. An additional absolute position mark 615 may also be used at decision point 404 to indicate a precise location where a carrier needs to initiate a turn or otherwise interact with decision point 404. If the carrier proceeds onto track section C, it can observe variations in the track surface to provide real-time trajectory estimates and any error in those estimates can be corrected. Upon observing synchronization mark 604, the carrier may correct any accumulated error in its position or use the first synchronization mark 604 to synchronize the expected position of subsequent synchronization marks. Position mark 630 can be in the form of an LED to indicate an important location within section C, for example.

Alternatively, if a carrier diverts onto section H at decision point 404, the carrier will also determine a real-time trajectory from observing the relative motion of the track surface and the carrier. Upon encountering synchronizations marks 606, any error accumulated in that estimate of the real-time trajectory of the carrier can be corrected.

It should be noted that, in some embodiments, synchronization marks are provided at regular intervals. By providing them at regular intervals, not only can they be used to calculate trajectories, but they may also be used to calibrate the position decoding sensors. For example, a processor extrapolating position information from observed changes in the image of the track surface can learn from the synchronization marks that a given degree of relative motion corresponds to a certain degree of actual motion in the real world. That is, a carrier can use the observed error to anticipate future error and adjust its real-time calculation of trajectory. In other embodiments, image sensors used in position decoding sensors can be calibrated from the factory such that an observed image distance of a certain number of pixels is said to correspond to a given distance in the real world.

Proceeding along section H, when a carrier reaches a point at which it can interact with pipette 422, the carrier encounters another absolute position mark 620. Here, position mark 620 may be a QR code that includes data that identifies the position as relating to pipette 422. For example, the QR code may say "pipette 422." By providing additional information besides just a mark that indicates a seemingly arbitrary point on the track, the observing carrier can be guaranteed that it has reached the right absolute position within the track system by reading the QR code of its destination. It should be appreciated that the various types of absolute position marks shown and described with reference to FIG. 9 may be interchangeable.

FIGS. 10A and 10B show an alternate embodiment of the track sections shown in FIG. 9. In these examples, decision point 404 provides a line that a carrier can follow. For example, a carrier with a steering system can traverse the track system by continually following a longitudinal line that indicates the path it should follow. By following this line, which can be changed by an external controller, such as central controller 440 (FIG. 6), the carrier can navigate the track system without the need for mechanical gates. In this example, a carrier can follow a line 642, which may be a static line. For illustrative purposes, line 642 is shown as a dashed line, but a solid line, or any other suitable type of line may be used. Upon approaching decision point 404, a carrier will observe absolute position mark 610, which may be a QR code that identifies the upcoming decision point 404. This can be used to alert the carrier that a decision point is eminent and to adjust its trajectory accordingly.

If the carrier should navigate by turning, as represented in FIG. 10A, line 640 may be illuminated, turned on, or otherwise indicated to the carrier. In some embodiments, a rewritable electronic display, such as an E-ink display or an LCD display, can indicate line 640 as a line (shown as a dark line) for the carrier to follow. After traversing line 640, the carrier may encounter a static line 644, which, like line 642, may be permanently drawn on the surface of the track, such as by paint, sticker, or etching. Alternatively, line 642 and 644 may be dynamically displayed on the track.

If the carrier should navigate by proceeding straight, as represented in FIG. 10B, line 646 may be illuminated, turned on, or otherwise indicated to the carrier Like line 640, this indication may be via a rewritable electronic display, such as an E-ink display or LCD display.

In some embodiments, mark 610 is a rewritable landmark that also includes a rewritable electronic display. This can allow mark 610 to convey routing information to the carrier, which may indicate whether the carrier should turn, or go straight. In some embodiments, this may be done without requiring the dynamic drawing or highlighting of lines 640 and 646.

FIGS. 11A and 11B show the exemplary hardware that can be used in conjunction with position decoder 313 (see also FIG. 5) to observe marks, and the features of a track surface to determine trajectory and position information. As shown, a light source 702 can be provided in the form of an LED or other light source off axis from image sensor 704. By providing illumination off axis, which may include illumination at a steep angle relative to surface 708, the light source 702 can create shadows within surface 708 to accentuate any surface textures. Image sensor 704, which may include optics, such as lenses to properly observe the image of track surface 708, captures images of the surface at regular intervals in real time. Image processor 706 may be coupled to image sensor 704 to decode the signals from image sensor 704 and provide image data to position decoder 313.

Image processor 706 or position decoder 313 may include suitable processors and software for extrapolating salient features from the image data. Suitable processors can include CPUs, GPUs, DSPs, APUs, ASICs, or any other suitable circuitry to process the image. Once an image is processed, it can be compared to successive or predecessor images to find similar features for comparison. These features can be compared to determine a pixel distance to indicate how much the feature has moved between successive images. The images can also be compared to create a plurality of pixel motion vectors within the comparison of the image, which can be averaged to determine a trajectory between the two images. By using multiple successive images, any quantization error in the pixel distance between images can be corrected, such as by averaging.

In the example shown in FIG. 11A, image sensor 704 observes the texture of track 708 between marks. As can be seen, as the carrier and, by extension, the image sensor 704, move to the right, image sensor 704 will observe position mark 601. Upon encountering position mark 601, position decoder 313 can compare successive images to determine the exact position of the center of position mark 601 relative to the body of the carrier. For example, successive images can be compared to determine which image is closest to centering position mark 601 within the image, which indicates the particular time at which image sensor 704 traversed the known location of the center of absolute position mark 601. In this manner, image sensor 704 can be used to determine the precise location of the carrier within the track system when it traverses an absolute position mark (such as mark 601).

In the example shown in 11B, a dynamic position mark 710 can be observed by image sensor 704. This dynamic position mark 710 can be, for example, a QR code created by an electronically rewritable surface. This electronically rewritable surface can be any suitable rewritable surface, such as an E-ink display, an LCD display, an AMOLED or OLED panel, or an array of LEDs. In some embodiments, the size of a position mark can be larger than the image field of sensor 704. Because image sensor 704 moves longitudinally, the length of a position mark can still be observed using a smaller imaging sensor because the imaging sensor will eventually traverse the entire mark. To the extent that a position mark is wider than the image field of an imaging sensor, multiple image sensors may be employed and the images can be stitched together. It is contemplated that multiple imaging sensors can be used in certain embodiments to provide added robustness of observing textures (e.g., providing stereoscopic or redundant vision) or position marks. Multiple imaging sensors, such as an array of imaging sensors, can also be used to observe larger position marks, while also providing robustness in observing real-time relative motion of the track surface to the carrier. In some embodiments, a separate image sensor or sensors may be used to read marks, while another sensor may be used to observe the relative motion of the track surface.

Electronically rewritable position mark 710 can be operated via a controller 712, which may provide parallel or serial communication to transistors driving each pixel, such as by providing row and column data. Controller 712 may be responsive to a processor, such as central control processor 440, which can allow a central processor to choose which information to convey to a given carrier on a real-time basis. The processor 440 may be responsive to instructions and data in memory 714, which may include a database of potential QR codes as well as a database of carrier information to determine what general information to display, and how to display it. In some embodiments, the processor used to interact with controller 712 is a local processor that is separate from central control processor 440, and may, in some embodiments, be responsive to central control processor 440.

Figure 12:
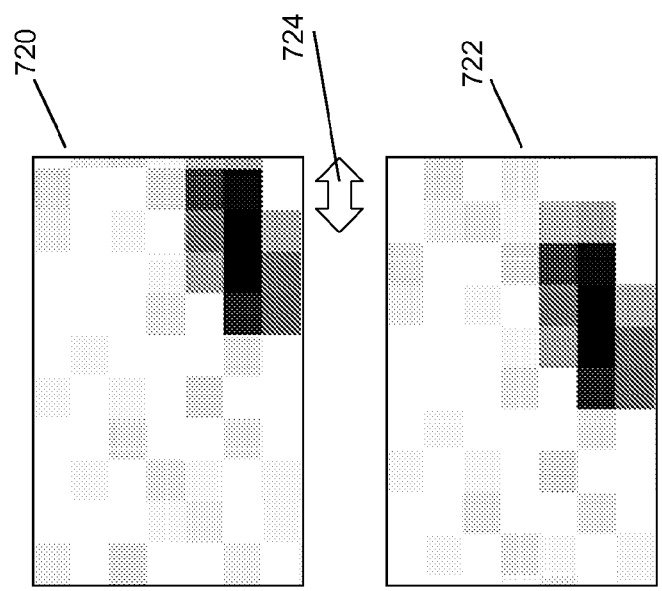
FIG. 12 is an exemplary comparison of successive images for use with certain embodiments.

FIG. 12 shows an example of comparing successive images to observe textures in the track surface and to determine trajectory information. This comparison may be done via position decoder 313, or any imaging subsystem controlled by, or interacting with, position decoder 313, such as image processor 706. As shown in this example, a first image 720 shows grayscale pixel data relating to an observed texture in the track surface. In this example, a low-resolution image sensor is used. Darker pixels may indicate that a shadow is being cast by a local dip or scratch in the track surface. The next frame captured by image sensor 704 is illustrated by second image 722. As can be seen in a side-by-side comparison of these two frames, the image in first image 722 has moved approximately 2 pixels to the left when viewed in second image 722 (represented by arrow 724). This two-pixel difference provides a local estimate of the instantaneous trajectory of the carrier. That is, because the track surface is not moving, any detected motion in the images indicates the motion of the carrier.

The successive comparison of image 720 with successive image 722 can be repeated, while the carrier traverses portions of the track without encountering absolute position marks. By averaging the observed motions, a fairly accurate determination of the real-time trajectory of the carrier can be created. In some embodiments, this comparison is repeated a predetermined number of times during a giving time period—e.g., 1000 times per second.

Figure 13:
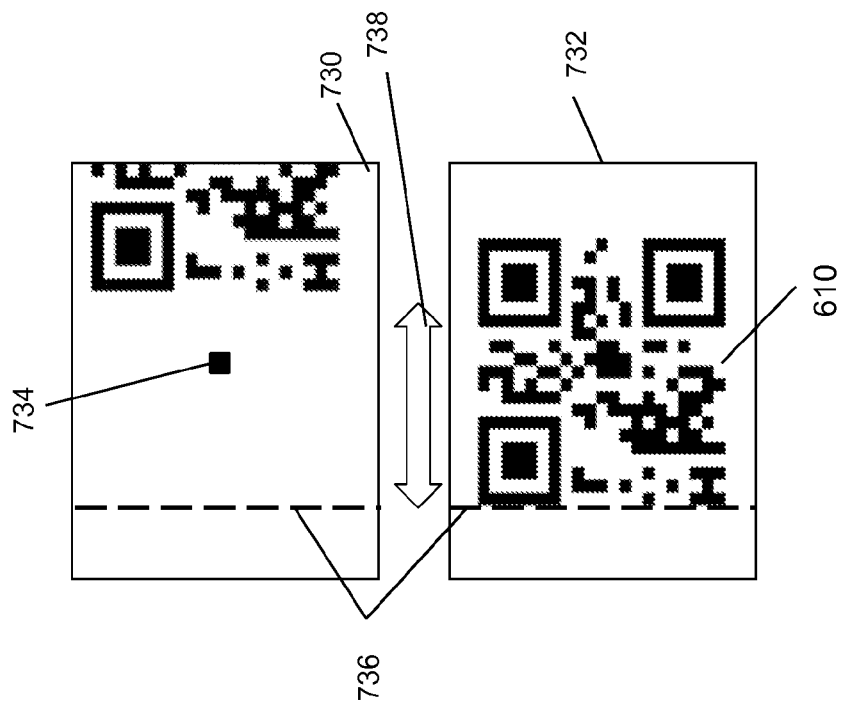
FIG. 13 is an exemplary comparison of successive images for use with certain embodiments.

FIG. 13 shows successive images 730 and 732 at position mark 610. Image 730 shows the leading edge of position mark 610. In a first frame, image 730 only shows part of the information of mark 610. However, certain salient features, such as the large concentric boxes, can be an indication that the carrier is approaching a position mark. The position decoder can employ a reticle, such as line 736 and center pixel 734, to determine the position or orientation of the mark 610 within the image plane. The reticle can be virtual (e.g., applying significance to certain pixels), or can employ some form of optical indication of the center point of the image. In image 730, the center of mark 610 is not aligned with the reticle, and the position decoder can choose not to update its absolute position until successive frames.

In successive frame 732, absolute position mark 610 is properly aligned with the reticle of the image. Here, the image sensor can use the relative motion of position mark 610, indicated by arrow 738, to convey instantaneous trajectory information, but may also use the alignment of position mark 610 with the reticle to convey absolute position information. When the mark is aligned with the reticle, the absolute position of the carrier is synchronized with the absolute position of mark 610. It is also contemplated that, where the mark does not align with a center point in the image, the offset can be calculated so that position decoder 313 can determine an absolute position, even where a virtual reticle in the image does not fully align with an absolute position mark in the track surface.

As mentioned above, certain image sensors may not have the proper aspect to see the entirety of a position mark at a given moment. For example, a series of successive images may capture all the information of a QR code, even though an individual image sensor is incapable of viewing the entire QR code in a single frame. These successive frames can be stitched together to glean the entirety of the information in the QR code, or other position mark. It should be appreciated that adjacent images in time or adjacent images in space, where multiple image sensors are used, can be stitched together by overlapping common features to create a whole image of a given position mark. This stitched mark can be used in the same manner as the mark 610, shown in FIG. 13.

FIG. 14 shows some examples of absolute position marks that may be suitable for certain embodiments of the present invention. QR code 740 is a version 1 QR code including the phrase "position 45." Such an absolute position mark can be used to indicate an identification of a given position, so that the identification of an absolute position, along with the location of an absolute position, can be conveyed to the carrier. QR code 742 is an absolute position mark containing the phrase "pipette 3." This exemplary position mark can be used at destinations for carriers, such as a position accessible to pipette 3, and can convey both the identification of the position and the precise location of the position. Other QR codes can contain dynamic routing information or other information to be conveyed to a carrier. These position marks are suitable for electronically rewritable surfaces, where the content of the QR code can be dynamic, such that different carriers receive different messages within the absolute position mark formed by the QR code. For example, a first carrier can observe a QR code and a successive carrier can be shown a different QR code (or other mark suitable for conveying data) that identifies the current position and identifies a different next position for the carrier to navigate to.

Position mark 744 is a barcode. A barcode works in substantially the same way as a QR code, but in one dimension. A barcode can use certain marks (e.g., a leading mark or a fixed bold mark within the code) within the overall barcode to indicate a one-dimensional absolute position. The barcode can also convey certain data, such as an identification of the position, by using the content of the barcode.

Position mark 746 is a bulls-eye mark, which is a symmetric two-dimensional mark suitable for indicating an absolute position in two dimensions, but may not be suitable for conveying other information. Position mark 750 is a cross. Like the bulls-eye, the cross is symmetric, and conveys little orientation information or data. Marks 752 and 754 are examples of simple position marks that convey position and orientation due to asymmetry but, unlike QR codes or barcodes, can only convey a limited amount of other data (e.g., one to three bits), if any. These simpler marks may be suitable for embodiments where a carrier has other means for receiving information, such as near-field/RF communication or a wireless antenna. Simpler marks may be advantageous in that they may allow a carrier to employ simpler optics and image processing, which may be cheaper.

FIG. 15 shows some examples of absolute position marks in the context of synchronization marks. Zooming out from a track surface, there may be a large number of synchronization marks 602 repeated at regular intervals, such as every 10 or 20 cm, while absolute position marks 740, 746, and 750 in tracks 760, 762, and 764, respectively, provide an absolute position within the track. In this manner, synchronization marks 602 can be viewed as repeating offsets from a given absolute position.

Figure 16:
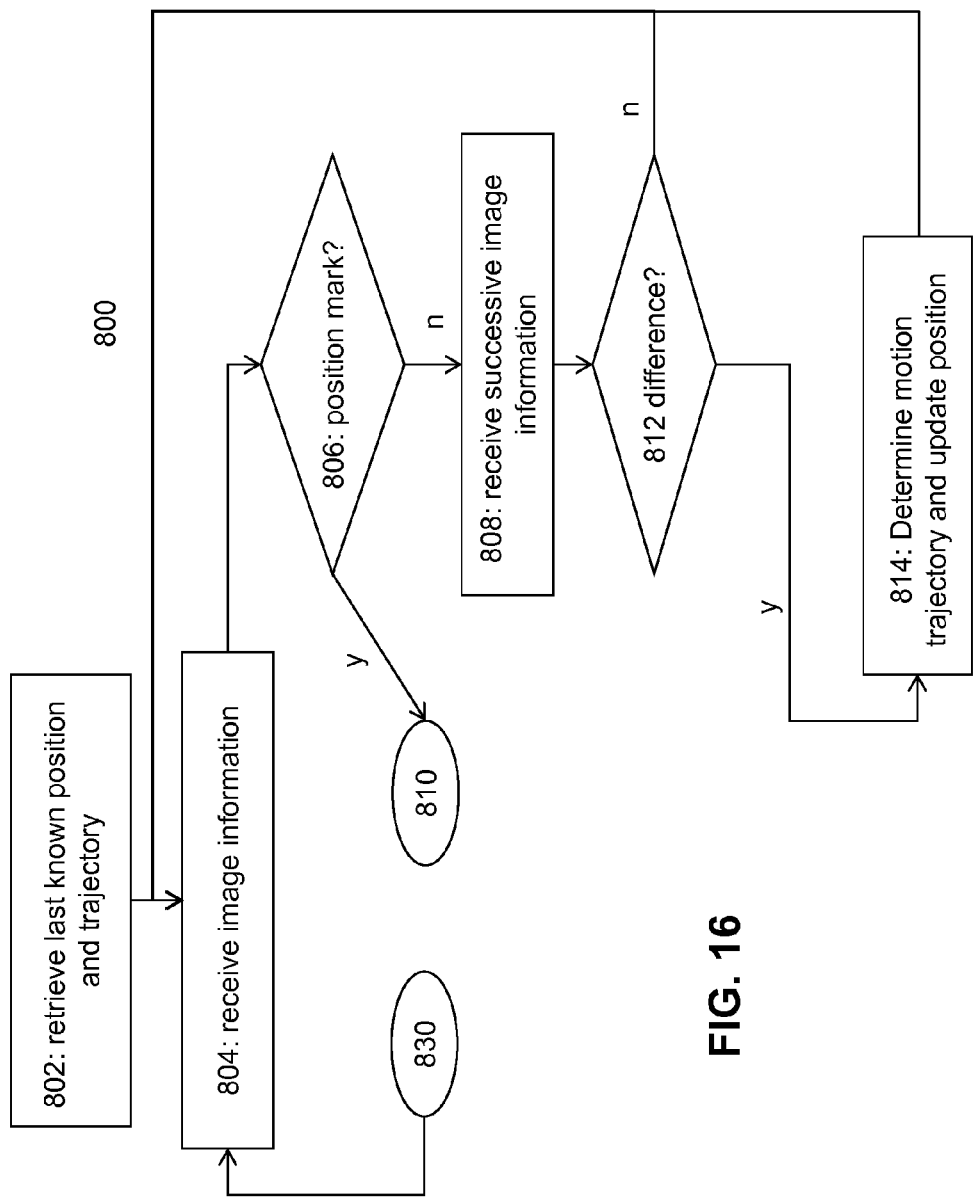
FIG. 16 is a flowchart of an exemplary algorithm for observing the relative motion of a track surface for use with certain embodiments.

FIG. 16 shows an exemplary method 800 for observing the track surface to determine instantaneous trajectory, as well as for observing position marks on the track surface. At step 802, the carrier retrieves the last known position and trajectory of the carrier. This provides a baseline for adjusting the trajectory based on new image information. At step 804, the imaging devices on the carrier receive image information about the track surface. This can include an image of the local track surface that has been illuminated at a steep angle via a light source onboard the carrier.

Figure 17:
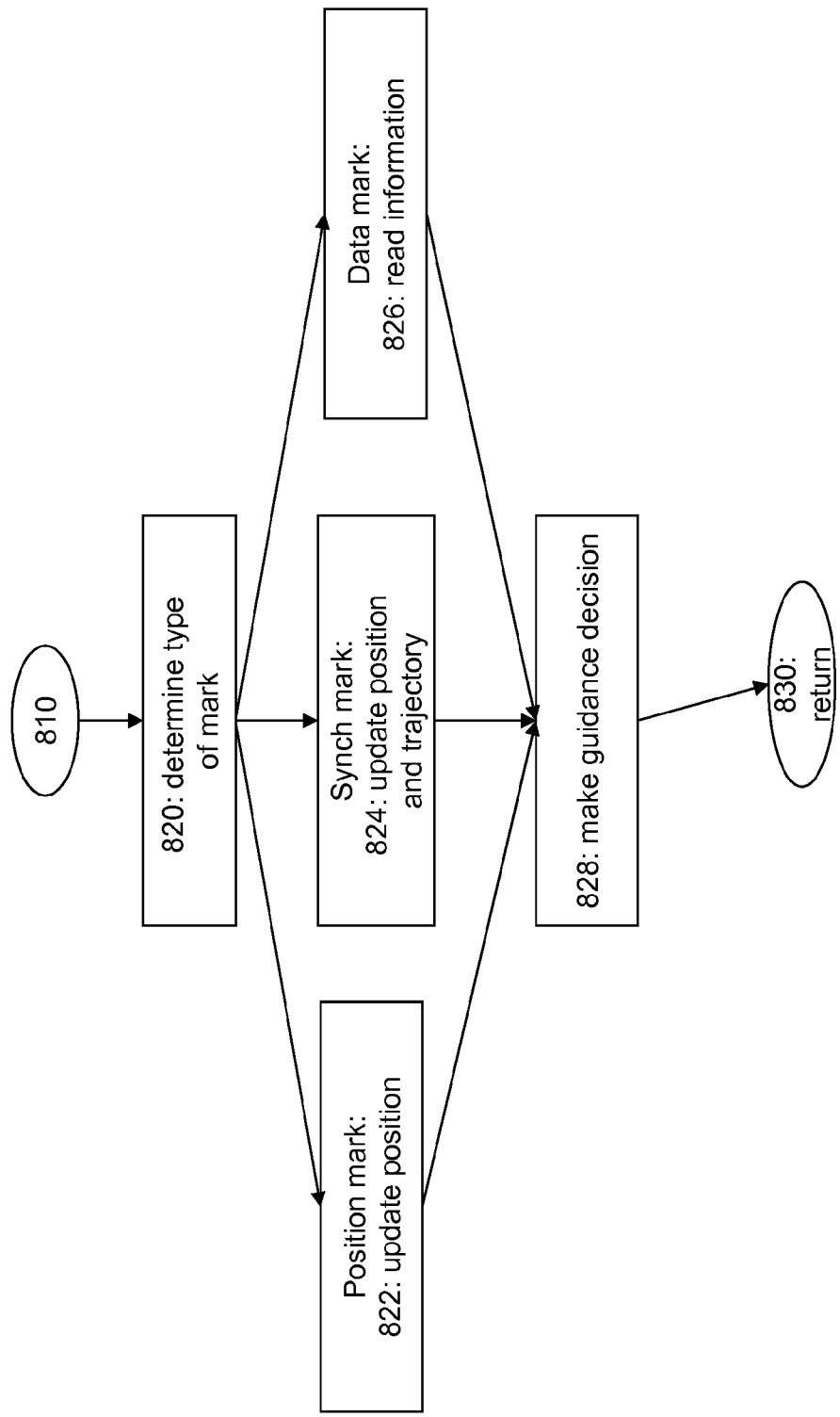
FIG. 17 is a flowchart of an exemplary algorithm for interpreting position marks for use with certain embodiments.

At step 806, the images are processed by the carrier to determine if one or more features in the image indicate the presence of a position mark. For example, very dark features may indicate that a position mark is in the image. These features can then be compared to expected features of a position mark to determine if the image contains a position mark. If the position mark is identified, the method proceeds to step 810, which is shown in FIG. 17. If no position mark is detected, the carrier proceeds to compare successive images to determine the relative motion of the track surface to determine an instantaneous trajectory of the carrier.

At step 808, a successive image is gathered using one or more image sensors of the carrier. At step 812, images are processed to compare the relative motion of pixels or features within the images. If there is a difference, the position of the carrier can be updated by extrapolating the change in position from the previous known position and the difference between images determined at step 814. If the instantaneous velocity between the two images deviates from the expected trajectory, the trajectory can also be updated. If there is no difference between the successive frames, this can indicate that the carrier has stopped. If this is a change in the expected trajectory, the trajectory can be updated, while the position will remain the same. The method then returns to step 804, so that additional images can be retrieved and compared. In this manner, the observation of the relative motion of the track surface continues until position marks are encountered. This provides real-time trajectory information that can be dynamically observed between position marks.

FIG. 17 shows an exemplary method for handling position marks that are observed in images of the track surface. At step 810, the carrier initiates the position mark interpretation process 820. At step 820, the carrier observes the image data, which may include multiple images related in time or space to determine if the mark in the image corresponds to a known type of mark. If the determined type of mark is a position mark, such as an absolute position mark or landmark, the position information of the carrier can be updated at step 822. For example, if a carrier believes it is at position 44, and the absolute position mark indicates that the position is actually position 45, the carrier can replace its calculated position with the information in the absolute position mark.

If the observed marking is a synchronization mark, at step 824, the position and trajectory information can be updated/rectified using the mark. For example, if the carrier was not expecting a synchronization mark for another centimeter, the appearance of a synchronization mark can indicate that the calculated trajectory has led to an error (e.g., a 1 cm error). The trajectory can be adjusted using this information, and the determine position can also be adjusted to synchronize the calculated position with the position of the synchronization mark.

If the mark is determined to be a type of mark that contains data, such as a QR code, which can simultaneously be a position mark or synchronization mark, this data is read at step 826. The reading of this data can be in addition to updating position and trajectory information at step 822 or 824. This data can be, for example, an identification of the current position, which may be useful for rectifying the absolute position of the carrier, or can include dynamic routing instructions or other information, such as an identification of the current track section.

Once the carrier has updated information gleaned from the marks encountered, the carrier can make guidance decisions at step 828. For example, determining that a mark encountered indicates the destination position of the carrier, a carrier may stop. Similarly, if a mark indicates that a decision point is coming, the carrier may slow down and/or prepare to turn. If the mark includes new routing instructions, the carrier can update its navigation and adjust its trajectory to begin navigating to a new destination.

At step 830, the carrier exits the mark interpretation method and returns to step 804 of FIG. 16.

While the invention has been described with respect to transporting samples, the methods and systems discussed herein can also be used to transport other items in an IVD environment. For example, the item being transported can be a patient sample, one or more reagents for use with sample analysis, or waste products, such as spent reagent cartridges, used samples, or the like. Reagents can be transported on carriers that are similar to those used for transporting samples. In some embodiments, the bracket supporting the item, such as bracket 262 in FIG. 4A, is adapted to the item being transported. For example, the bracket can be molded to receive a reagent cartridge and securely transport it around the automation system between stations, such as a reagent storage station and a testing station, where the testing station can use the reagent. It should be appreciated that carriers can be adapted to transport any suitable item using the methods and systems described herein.

Embodiments of the present invention may be integrated with existing analyzers and automation systems. It should be appreciated that carriers may be configured in many shapes and sizes, including layouts and physical configurations suitable for use with any contemplated analyzer or instrument. For example, in some embodiments, a carrier may include multiple slots for carrying multiple samples around an automation track. One embodiment, for example, may include a physical layout of a tube-holding portion of a carrier with multiple slots in one or more transport racks. Each rack may include multiple slots (e.g., five or more slots), each slot configured to hold a tube (e.g., a sample tube).

Although the invention has been described with reference to exemplary embodiments, it is not limited thereto. Those skilled in the art will appreciate that numerous changes and modifications may be made to the preferred embodiments of the invention, and that such changes and modifications may be made without departing from the true spirit of the invention. It is therefore intended that the appended claims be construed to cover all such equivalent variations that fall within the true spirit and scope of the invention.

What is claimed:

1. An automation system for use with an automated clinical chemistry analyzer comprising:
    a track having a first surface with a surface texture;
    at least one independently movable carrier configured to independently move along the first surface and optically observe a relative motion of the first surface to determine a trajectory of the at least one independently movable carrier, using at least one sensor onboard the carrier that captures light reflected from the surface texture of the first surface; and
    one or more marks on the first surface that indicate absolute position information on the track.

2. The automation system of claim 1, wherein the one or more marks comprise at least one QR code.

3. The automation system of claim 1, wherein the one or more marks comprise at least one barcode.

4. The automation system of claim 1, wherein the one or more marks comprise at least one two-dimensional mark.

5. The automation system of claim 4, wherein the two-dimensional mark is asymmetric.

6. The automation system of claim 1, wherein at least one independently movable carrier is further configured to:
    illuminate the first surface;
    observe successive images of the first surface; and
    compare successive images to determine at least one of a direction and a magnitude of the relative motion.

7. The automation system of claim 1, wherein at least one independently movable carrier comprises:
    a light source;
    an image sensor; and
    at least one processor configured to detect relative motion within a plurality of successive images captured by the image sensor.

8. The automation system of claim 1, wherein the first surface further comprises a plurality of synchronization marks and the at least one independently movable carrier is further configured to use the plurality of synchronization marks to correct errors in the determined trajectory information for the at least one independently movable carrier.

9. The automation system of claim 1, wherein the one or more marks comprise one or more static images on the first surface.

10. A carrier configured to travel along a track having a first surface, having a surface texture for use with an automated clinical chemistry analyzer, the carrier comprising:
    a light source configured to illuminate the first surface;
    an image sensor, onboard the carrier, for capturing images of the first surface, illuminated by the light from the light source; and
    at least one processor configured to detect a relative motion of the surface texture of the first surface by comparing a plurality of successive images captured by the image sensor, wherein the relative motion corresponds to a trajectory of the carrier.

11. The carrier of claim 10, wherein the carrier is further configured to adjust the trajectory in response to the relative motion.

12. The carrier of claim 10, wherein the carrier is further configured to observe one or more marks on the first surface to determine an absolute position along the track.

13. The carrier of claim 12, wherein the carrier is further configured to obtain non-positional data from the one or more marks on the first surface.

14. The carrier of claim 10, wherein the carrier is further configured to utilize the relative motion to determine a substantially real-time position of the carrier along the track.

15. The carrier of claim 14, wherein the carrier is further configured to observe one or more synchronization marks on the first surface of the track.

16. The carrier of claim 15, wherein the carrier is further configured to utilize the synchronization marks to adjust the determination of the substantially real-time position of the carrier.

17. The carrier of claim 10, wherein the carrier is further configured to follow a visible line on the first surface of the track.

18. A method for transporting items in an in-vitro diagnostics (IVD) environment comprising the steps of:
    illuminating a first surface of a track along which one or more independently movable carriers move, wherein each carrier is configured to hold one or more fluid vessels;
    observing successive images of the first surface using an imaging sensor, onboard each of the one or more independently movable carriers;
    comparing successive images, using at least one processor, to determine a direction and a magnitude of the relative motion of the carriers; and
    determining an absolute position of at least one of the carriers by detecting one or more reference marks on the track surface.

19. The method of claim 18, wherein the items transported comprise fluid samples.

20. The method of claim 18, wherein the items transported comprise reagents.

* * * * *